United States Patent
Boesen

(10) Patent No.: US 8,140,357 B1
(45) Date of Patent: Mar. 20, 2012

(54) POINT OF SERVICE BILLING AND RECORDS SYSTEM

(76) Inventor: Peter V. Boesen, Des Moines, IA (US)

( * ) Notice: Subject to any disclaimer, the term of this patent is extended or adjusted under 35 U.S.C. 154(b) by 1053 days.

(21) Appl. No.: 09/558,519

(22) Filed: Apr. 26, 2000

(51) Int. Cl.
G06Q 50/00 (2012.01)
G06Q 40/00 (2012.01)

(52) U.S. Cl. ............................................. 705/3; 705/4

(58) Field of Classification Search .................. 705/2–4, 705/34, 40, 1, 22, 24, 17; 600/300, 301, 600/435, 587; 707/104.1, 2, 102; 704/9; 235/375; 345/156, 163, 419, 173; 379/126, 379/201.1; 715/745, 765, 766
See application file for complete search history.

(56) References Cited

U.S. PATENT DOCUMENTS

| | | | | |
|---|---|---|---|---|
| 5,229,584 A * | 7/1993 | Erickson | ...................... | 235/375 |
| 5,325,293 A * | 6/1994 | Dorne | ............................ | 705/2 |
| 5,404,292 A * | 4/1995 | Hendrickson | .................. | 600/301 |
| 5,471,382 A * | 11/1995 | Tallman et al. | ............... | 600/300 |
| 5,561,446 A * | 10/1996 | Montlick | ...................... | 345/173 |
| 5,772,585 A * | 6/1998 | Lavin et al. | .................... | 600/300 |
| 5,778,345 A * | 7/1998 | McCartney | ...................... | 705/2 |
| 5,823,949 A * | 10/1998 | Goltra | .......................... | 600/300 |
| 5,867,821 A | 2/1999 | Ballantyne et al. | | |
| 5,915,240 A | 6/1999 | Karpf | | |
| 5,924,074 A | 7/1999 | Evans | | |
| 5,953,704 A | 9/1999 | McIlroy et al. | | |
| 5,970,463 A * | 10/1999 | Cave et al. | ......................... | 705/3 |
| 6,000,828 A * | 12/1999 | Leet | ................................ | 705/2 |
| 6,047,259 A | 4/2000 | Campbell et al. | | |
| 6,088,677 A * | 7/2000 | Spurgeon | ........................ | 705/4 |
| 6,094,492 A | 7/2000 | Boesen | | |
| 6,112,183 A | 8/2000 | Swanson et al. | | |
| 6,125,350 A | 9/2000 | Dirbas | | |
| 6,154,726 A | 11/2000 | Rensimer et al. | | |
| 6,192,345 B1 * | 2/2001 | Chicorel | ........................... | 705/3 |
| 6,324,516 B1 * | 11/2001 | Shults et al. | ...................... | 705/2 |
| 6,338,039 B1 * | 1/2002 | Lonski et al. | ..................... | 705/3 |
| 6,347,329 B1 * | 2/2002 | Evans | ............................ | 709/202 |
| 6,370,511 B1 * | 4/2002 | Dang | ............................... | 705/3 |
| 6,393,404 B2 * | 5/2002 | Waters et al. | ..................... | 705/2 |
| 6,408,081 B1 | 6/2002 | Boesen | | |
| D464,039 S | 10/2002 | Boesen | | |
| 6,470,893 B1 | 10/2002 | Boesen | | |
| D468,299 S | 1/2003 | Boesen | | |
| D468,300 S | 1/2003 | Boesen | | |
| 6,542,721 B2 | 4/2003 | Boesen | | |

(Continued)

OTHER PUBLICATIONS

Terdoslavich, William, "Writing an Rx for doctors' woes", Computer Reseller News, Jan. 29, 1996, No. 668, p. SS17.*

(Continued)

*Primary Examiner* — Gerald J. O'Connor
*Assistant Examiner* — Natalie A Pass
(74) *Attorney, Agent, or Firm* — McKee, Voorhees & Sease, P.L.C.

(57) ABSTRACT

A billing and records system software application that places responsibility for billing and coding accuracy upon the provider of services and is used on a front-end computer which allows the provider to update, edit, and input data. The front-end computer is linked to a back-end computer. The back-end computer program stores the necessary databases for use on the front-end computer. The reference databases have all of the current coding required for the provider. The back-end computer also contains a linkage component and a billing program which uses data from the front-end computer to prepare a bill for the encounter.

7 Claims, 21 Drawing Sheets

U.S. PATENT DOCUMENTS

| | | | |
|---|---|---|---|
| 6,560,468 | B1 | 5/2003 | Boesen |
| 6,611,846 | B1* | 8/2003 | Stoodley ................... 707/104.1 |
| 6,664,713 | B2 | 12/2003 | Boesen |
| 6,694,180 | B1 | 2/2004 | Boesen |
| 6,718,043 | B1 | 4/2004 | Boesen |
| 6,738,485 | B1 | 5/2004 | Boesen |
| 6,738,754 | B1* | 5/2004 | Norman, Jr. ...................... 707/2 |
| 6,738,784 | B1* | 5/2004 | Howes ....................... 707/104.1 |
| 6,754,358 | B1 | 6/2004 | Boesen |
| 6,784,873 | B1 | 8/2004 | Boesen |
| 6,823,195 | B1 | 11/2004 | Boesen |
| 6,852,084 | B1 | 2/2005 | Boesen |
| 6,879,698 | B2 | 4/2005 | Boesen |
| 6,892,082 | B2 | 5/2005 | Boesen |
| 6,915,254 | B1* | 7/2005 | Heinze et al. ..................... 704/9 |
| 6,920,229 | B2 | 7/2005 | Boesen |
| 6,952,483 | B2 | 10/2005 | Boesen |
| 2002/0007285 | A1* | 1/2002 | Rappaport ........................ 705/2 |
| 2002/0057810 | A1 | 5/2002 | Boesen |
| 2002/0087533 | A1* | 7/2002 | Norman, Jr. ...................... 707/3 |
| 2002/0118852 | A1 | 8/2002 | Boesen |
| 2003/0167189 | A1* | 9/2003 | Lutgen et al. ..................... 705/3 |
| 2004/0160511 | A1 | 8/2004 | Boesen |
| 2005/0043056 | A1 | 2/2005 | Boesen |
| 2005/0125320 | A1 | 6/2005 | Boesen |
| 2005/0148883 | A1 | 7/2005 | Boesen |
| 2005/0165285 | A1* | 7/2005 | Iliff ............................... 600/300 |
| 2005/0196009 | A1 | 9/2005 | Boesen |

OTHER PUBLICATIONS

Guadagnino, Christopher, "Documentation and coding tools", Physicians News Digest, Jun. 1998, 10 pages.*

IBM Visualization Data Explorer QuickStart Guide, 1997. (Retrieved from Internet Dec. 9, 2006) URL: <http://opendx.npaci.edu/docs/pdf/quickguide.pdf>.*

Medical Manager letter, Feb. 22, 2000, pp. 1-2.

Medical Manager Network Services Feature and Reports, Nov. 14, 1997, pp. 1-221.

Thomas R. O'Connell, *Tiny Computers Come in Handy, Doctors Find*, Des Moines Register, pp. 1B, 4B, Des Moines, IA.

Version 9 System Features Enhancements Manual and Training Guide, Apr. 2, 1998, pp. 8-23, 28-34, 38-41, 44-49, 56-63, and 80-81, South Bend, IN.

*Complete Steps to EMC Billing/MMNS*, Medical Manager Instruction Sheets, Feb. 2, 1999, pp. 1-3, South Bend, IN.

*Complete Steps to EPS STMTS/MMNS*, Medical Manager Instruction Sheets, Feb. 2, 1999, pp. 1, 2.

Medical Manager Network Services Mission Statement, Feb. 2, 1999, p. 1, South Bend, IN.

Medical Manager Network Services Features and Reports, Nov. 14, 1997, pp. 1-28, Mountain View, CA.

Medical Manager Network Services In-User Training, Oct. 30, 1997, pp. 14-40, 64-111, 143-170, Mountain View, CA.

Medical Manager Complete Listing of Features and Reports, Apr. 14, 1997, pp. 1-22, 31, 41-43, 49-54, 56-60, 67, 82, 90-92; 108, 123-138, 144-145, Mountain View, CA.

Medical Manager Integrated Practice Management Solutions Manual, Winter 2000, pp. iii-ix, 1-1, 12-1, 12-10-12-17, Mountain View, CA.

Medical Manager Integrated Practice Management Solutions New System Features Manual, Oct. 30, 1997, pp. 19-20, 31, 32, 56-73, 78-85, 92-97, 117-120, 122, 123, and 126, Mountain View, CA.

Timekeeping Contents, Omega Legal Systems, pp. 1-6, Phoenix, AZ.

Cash Receipts Contents, Omega Legal Systems, pp. 1-10, Phoenix, AZ.

Accounts Payable Contents, Omega Legal Systems, Oct. 29, 1998, pp. 1-16, Phoenix, AZ.

Billing Cycle Procedures, Omega Legal Systems, Oct. 21, 1998, pp. 1-6, Phoenix AZ.

Program Information, Version 5.2, Omega Legal Systems, Nov. 1998, pp. 1-8, Phoenix, AZ.

Getting Started, Version 5.2, Omega Legal Systems, Nov. 1998, pp. 1-8, Phoenix, AZ.

Voice Sound Transmission Apparatus, System and Method Including Cradle, U.S. Appl. No. 09/640,230, filed Aug. 16, 2000, Boesen, Dr. Peter V.

Cellular Telephone, Personal Digital Assistant and Pager Unit with Capability of Short Range Radio Frequency Transmissions, U.S. Appl. No. 10/359,757, filed Feb. 6, 2003, Boesen, Dr. Peter V.

Voice Transmission Apparatus With UWB, U.S. Appl. No. 11/151,083, filed Jun. 13, 2005, Boesen, Dr. Peter V.

Voice Communication Device, U.S. Appl. No. 11/243,286, filed Oct. 4, 2005, Boesen, Dr. Peter V.

Cellular Telephone, Personal Digital Assistant with Dual Lines for Simultaneous Uses, U.S. Appl. No. 09/886,526, filed Jun. 21, 2001, Boesen, Dr. Peter V.

Cellular Telephone, Personal Digital Assistant with Dual Lines for Simultaneous Uses, U.S. Appl. No. 11/117,686, filed Apr. 27, 2005, Boesen, Dr. Peter V.

Method and System for Purchasing Access to a Recording, U.S. Appl. No. 10/842,207, filed May 10, 2004, Boesen, Dr. Peter V.

Method and System for Purchasing Access to a Recording, U.S. Appl. No. 11/222,014, filed Sep. 8, 2005, Boesen, Dr. Peter V.

Point of Service Billing and Records System, U.S. Appl. No. 09/558,519, filed Apr. 26, 2000, Boesen, Dr. Peter V.

Ultra Short Range Communication with Sensing Device and Method, U.S. Appl. No. 10/986,541, filed Nov. 11, 2004, Boesen, Dr. Peter V.

Voice Communication Device with Foreign Language Translation, U.S. Appl. No. 10/022,022, filed Dec. 13, 2001, Boesen, Dr. Peter V.

"Episode Treatment Groups: An Illness Classification and Episode Building System"; Symmetry, Health Data Systems Inc., 2004.

* cited by examiner

Please Select a Patient:

| Last Name | First Name | MI | Date of Birth | Provider | Encounter | Date | Appt. | Account No. | Action | Result |
|---|---|---|---|---|---|---|---|---|---|---|
| Barnes, Terry | | L | 12/22/66 | 1 | 30032 | 2/5/00 | 2:00 | 100 | S | X |
| Bond, James | | K | 10/22/74 | 1 | 30031 | 2/5/00 | 10:00 | 700 | S | X |
| Bondman, Robert | | V | 8/21/60 | 1 | 30010 | 2/5/00 | 12:45 | 6790.1 | S | X |
| Brown, Linda | | F | 2/3/78 | 1 | 31020 | 2/5/00 | 1:45 | 900 | S | X |
| Burk, Heather | | A | 10/2/43 | 1 | 31009 | 2/5/00 | 1:00 | 800 | S | X |
| Carpenter, Alicia | | A | 10/21/60 | 1 | 31053 | 2/5/00 | 3:20 | 400 | S | X |
| Close, Jason | | M | 3/2/56 | 1 | 31052 | 2/5/00 | 11:35 | 70 | S | X |
| Cup, Mary | | L | 9/3/43 | 1 | 31055 | 2/5/00 | 9:00 | 20 | S | X |
| Douglas, Tom | | L | 10/2/73 | 1 | 31089 | 2/5/00 | 10:00 | 50 | S | X |
| Dunbar, Lisa | | V | 8/21/60 | 1 | 31070 | 2/5/00 | 12:45 | 7865.0 | S | X |
| Handley, Raymond | | L | 11/21/43 | 1 | 31072 | 2/5/00 | 6:00 | 300 | S | X |
| Harty, Scott | | V | 6/3/73 | 1 | 31098 | 2/5/00 | 1:00 | 99999 | * | |
| Jones, Martha | | Q | 1/13/78 | 1 | 31093 | 2/5/00 | 5:30 | 75 | | |
| Knight, Michele | | L | 8/8/73 | 1 | 31094 | 2/5/00 | 12:45 | 200 | S | X |
| Loftin, Adrian | | C | 8/23/60 | 1 | 31099 | 2/5/00 | 1:30 | 5678.1 | S | X |
| Martin, David | | P | 3/30/51 | 1 | 31067 | 2/5/00 | 12:00 | 80 | S | X |
| Mays, Kelly | | D | 10/1/67 | 1 | 31008 | 2/5/00 | 4:45 | 60 | S | X |
| McDonald, Alex | | A | 6/3/81 | 1 | 31903 | 2/5/00 | 11:45 | 100 | S | X |
| Moore, Rudy | | V | 11/22/60 | 1 | 31100 | 2/5/00 | 9:30 | 4533.0 | S | X |
| Schoor, Stacy | | L | 10/2/36 | 1 | 31007 | 2/5/00 | 12:13 | 30 | S | X |
| Smith, Emmet | | R | 3/30/51 | 1 | 31201 | 2/5/00 | 5:00 | 123 | S | X |
| Quail, Dan | | D | 4/6/72 | 1 | 31029 | 2/5/00 | 6:45 | 120 | S | X |

[OK] [Cancel] [Add a Patient] [Edit a Patient] [Send/Receive] [Help]

Place of Service: 3    Doctor's Office    [Change Place of Service]

Facility Selection Screen:

Place of Service Search:
- Inpatient Psych. Fac. - M
- Other Med./Surg. Fac. - O
- Ambulance - 9
- Military Treat. Fac. - 1
- Com. Mental Health Ct. - N
- Res. Treatment Cent. - C
- Skilled Nursing Fac. - 8
- Night Care Facility - 6
- St/Local Pub He Ctr - Y
- Ambulance-Air/Water - L
- Outpatient Hospital - 2
- Patient's Home - 4
- Emergency Room Hosp. - G
- Comp. OP Rehab. Fac. - e
- Spec. Treatment Fac. - D
- Nursing Home - 7
- Independent Lab. - A
- Day Care Facility - 5
- Ind. Kidney Dis Cent - F
- Rural Health Clinic - Z
- Psyc. Resid Treat Ctr. - 0
- Doctors Office - 3
- Inpatient Hospital - 1
- Birthing Center - H
- Comp Inpatient Rehab. - X
- Hospice - K
- Custodial Care Fa. - J Facility Search:
- Blood & Plasma Center
- Childrens Hospital
- Community Hospital
- Doctors Laboratory
- Health Clinic
- Jefferson Memorial Hosp.
- Lakeland Services
- Madison Central Surgery
- Madison Convalescent Home
- Madison General Hospital
- Madison Surgery Center
- Miramonte Nursing & Rest
- Northwest Office

[OK] [Cancel] [Help]

POINT OF SERVICE BILLING AND RECORDS SYSTEM

BACKGROUND OF THE INVENTION

1. Field of the Invention

The present invention relates generally to a billing and records system. More particularly, though not exclusively, the present invention relates to a code-driven computerized system for health care billing that places the responsibility for billing on the health care provider at the point of service. The present invention includes variations for other service industries in which it is desirable to place primary responsibility for billing and records keeping on the service provider. Other industries include, but are not limited to the fields of law, accounting, dentistry, architecture, and any other service-type industry where clients demand service providers be accountable for their time and services.

2. Problems in the Art

In 1966, the American Medical Association developed a system it calls Current Procedural Terminology (CPT). The CPT system is used by doctors and other health care providers to ensure uniformity in the description of services performed through the use of a common set of codes and descriptors. Unfortunately, the CPT is updated every year and in the year 2000 is expected to utilize 7,755 codes and descriptors. Such constant updating of so many codes requires care providers to spend countless hours ensuring the proper codes for services provided are being utilized correctly. With the passage of the Medicare Catastrophic Coverage Act of 1988, it became a mandatory requirement to use diagnostic coding of the International Classification of Diseases, $9^{th}$ Revision, Clinical Modification, (ICD-9CM) published by the Practice Management Information Corporation with a new revision available approximately September $15^{th}$ of each year. Proper coding is the essential component of billing systems in order to satisfy the needs of clients relative to insurance companies, health maintenance organizations, and federal government programs such as Medicare and Medicaid.

Currently, there are multiple medical billing systems in place in which a care provider, such as a doctor, nurse, or allied health care provider, must manually enter coded patient care data on paper sheets prior to placement into a computer system. A billing clerk or other non-care providing personnel is then required to convert codes into a patient specific bill. This procedure allows for too many errors and places the ultimate responsibility for proper billing of clients on clerks and other personnel instead of upon the provider of services. As the health care provider is legally responsible for their submitted codes, it is desirable to facilitate the proper coding and billing for the person performing the services, i.e. the care provider.

Prior art systems which have attempted to correct this situation have allowed care providers to input patient specific coding in various ways. One prior art method of properly coding patient services was to use a preprinted super bill, such as the DocuScan®. A super bill, as commonly known in the art, allows the care provider to simply select the appropriate codes for the services performed via a Scantron® type sheet. However, due to the great number of codes, the super bill only contains pre-selected codes. Any additional or supplemental codes must be entered and selected manually by the care provider or an assistant and manually transferred into the billing system. Further, the super bill requires the care provider to take time filling in circular indicators and finding exactly what codes should be marked for the services performed. Once completed by the care provider, the super bill is then submitted to other personnel and a patient specific bill is generated.

Still other prior art systems allow doctors to use a remote terminal and batch in, or download from a main terminal, all of the patient records for patients to be seen during the day. Upon download, the care provider can then input which services were performed for the patients on the remote terminal. At the end of the day, the care provider must then batch out, or upload to the main terminal, all the patient records in one action. Upon receiving the patient records, including the services performed, the main terminal can then be used to generate individual patient bills. This prior art system does not allow for the real-time generation of an individual bill or correction of erroneously selected codes prior to the patient's departure from the care provider's office. A further problem with such a prior art systems has been the inability to edit a patient's data once that data has been entered and before the data is transmitted or to input a new patient into the system at the point of care via the remote computer.

Still further yet, such systems doe not allow the care provider to easily customize the diagnosis and procedure code screens with those codes most frequently used in the care provider's particular practice or field of specialty; such customization would require additional programming with great cost in terms of time and money. Nor do the prior art systems permit the care provider to search on-line for a particular code.

As on-line, or Internet based health-care information is becoming more and more prevalent, and more and more patients are on-line, it is desirable to have a system which is capable of having an on-line presence. Currently, WebMD.com provides information on physicians, diseases, and other medically related fields. However, the site does not allow patients to review their records or billing on-line. Further, the site does not allow care providers to provide such information.

Finally, remote computer systems are currently limited to laptop or desktop units which are then hardwired into the walls at the point of care and thereby wired to the main terminal. This prevents the care provider from entering data from any location other than where the computer has been placed. It is therefore desirable to provide a wireless, light-weight remote terminal system which allows the care provider to freely roam about and enter data anywhere at the point of care. It is further desirable to be able to access the host system even when out of the care provider's home office. In short, these prior art systems lack the functions and flexibility to be of significant assistance to the care provider. It is therefore desirable to have a system which overcomes the deficiencies found in the prior art, solving the aforementioned problems.

There is therefore a need to have a computer system that places responsibility for individual patient or client information, services provided, and billing records with the service provider at the point of service and allows the service provider to provide the patient or client with a bill upon the patient's or client's departure. In a medical application, there is a need to have a code driven computer system which accomplishes the above.

FEATURES OF THE INVENTION

A general feature of the present invention is the provision of a billing and records system which overcomes the problems found in the prior art.

A further feature of the present invention is the provision of a billing and records system which is code driven.

Another feature of the present invention is the provision of a computer billing and records system which places responsibility for billing and record keeping on the service provider.

A further feature of the present invention is the provision of a wireless computer billing and records system.

A still further feature of the present invention is the provision of a billing and records computer system that allows the service provider to input data at the point of service.

A yet further feature of the present invention is the provision of a billing and records computer system that allows the service provider to input data through an integral on-screen keyboard, dedicated to the individual screens as necessary and useful.

Another feature of the present invention is the provision of a billing and records computer system which allows a service provider to generate a patient's or client's bill prior to the patient's or client's departure.

A still further feature of the present invention is the provision of a billing and records computer system that allows a service provider to download specified patient or client data to and from a back-end computer.

An additional feature of the present invention is the provision of selected lateral communication from one front-end system to another distinct front-end system.

An still further feature of the present invention is the provision of lateral communication from one terminal to another via a wireless linkage.

An additional feature of the present invention is the provision of lateral communication from one terminal to another via a hard wire linkage.

Another feature of the present invention is the provision of a computer billing and records system that uses a graphical user interface to interact with the service provider to provide a means for accessing patient or client record and billing information at the point of service.

An additional feature of the present invention is the provision of a billing and records computer system having time based or service based code screens which may be easily customized by the service provider.

A still further feature of the present invention is the provision of a billing and records computer system having diagnosis and procedure code screens easily customized by the service provider.

A yet further feature of the present invention is the provision of a billing and records computer system that permits a service provider to search on-line, by code number or code description, to identify and select a particular code.

A still further feature of the present invention is the provision of a billing and records computer system which provides access to service providers and patients or clients via the Internet.

These, as well as other features and advantages of the present invention, will become apparent from the following specification and claims.

SUMMARY OF THE INVENTION

The present invention generally comprises a computer billing and records system. In a preferred medical embodiment, the present invention includes a software application that is CPT and ICD-9CM code-driven and places responsibility for patient billing and record keeping on the care provider at the point of care. A software application residing on a remote computer is included which provides a graphical user interface for the care provider. The software application allows the care provider to input and edit individual patient data from the remote computer. Further, the software application allows the care provider to select the appropriate coding and allows the care provider to update the codes appropriately.

BRIEF DESCRIPTION OF THE DRAWINGS

FIG. 8 is a pictorial representation of the Patient Selection screen.

FIG. 9 is a pictorial representation of the Facility Selection screen.

FIG. 12 is a pictorial representation of the Patient Procedure and Diagnosis screen.

FIG. 13 is a pictorial representation of the Diagnosis Codes screen.

FIG. 16 is a pictorial representation of the Ailment screen.

FIG. 17 is a pictorial representation of the Referring Provider List screen.

FIG. 26 is a pictorial representation of the View Practice Data screen.

FIG. 27 is a pictorial representation of the Color Preference screen.

DETAILED DESCRIPTION OF THE PREFERRED EMBODIMENT(S)

The present invention will be described as it applies to its preferred medical embodiment. It is not intended that the present invention be limited to the described embodiment. It is intended that the invention cover all modifications and alternatives which may be included within the spirit and scope of the invention.

Figure 1:
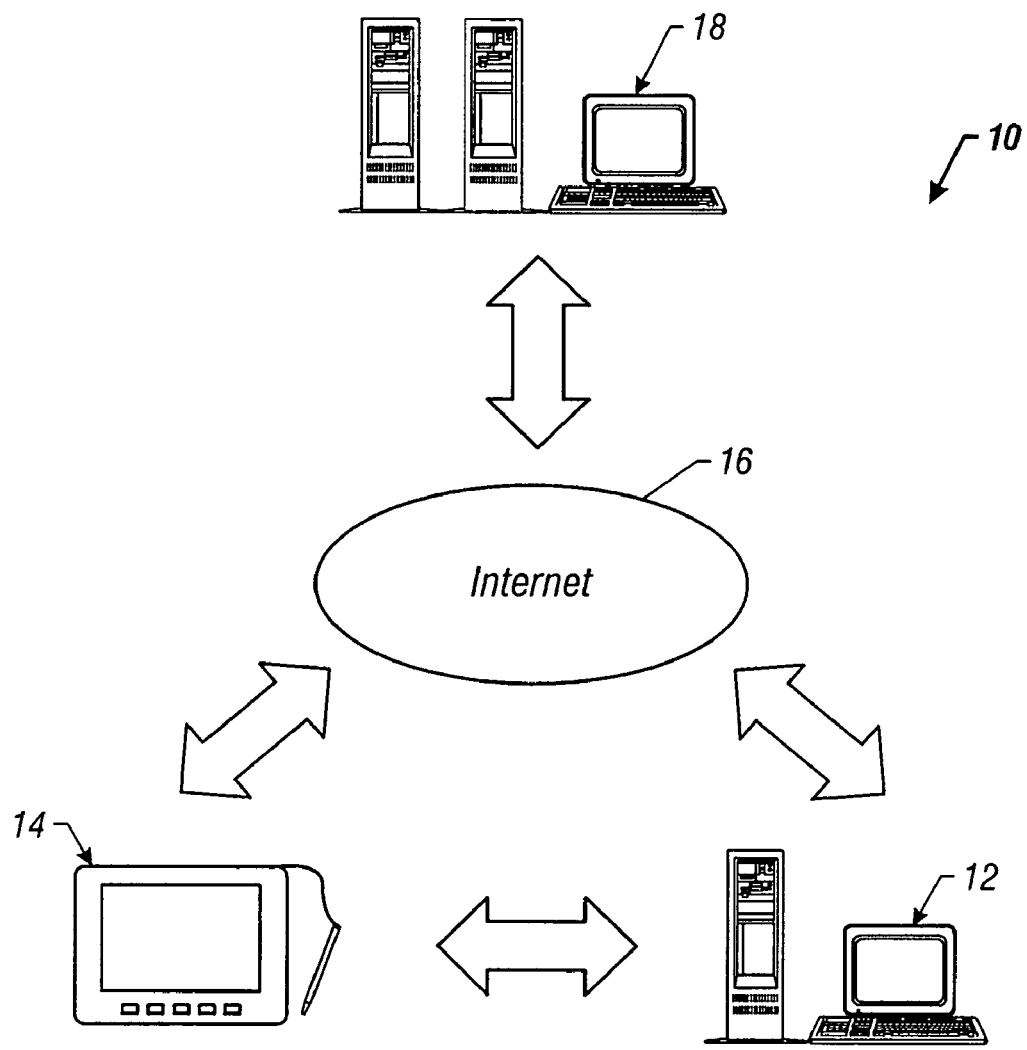
FIG. 1 is a pictorial representation of the network connectivity set-up of the preferred embodiment of the present invention.

As shown in FIG. 1, the billing and records system 10 of the present invention is a front-end-back-end system, with an open standards-based software architecture as is commonly known in the art. A new trend in such architecture is "multi-tiered solutions." A tier is simply a layer, usually consisting of a particular piece of software. For instance, in a typical front-end/back-end relationship, the front-end is one tier and the back-end is another tier. The front-end performs user interface services such as entering, editing, validating, and displaying information on the front-end computer 14 as shown in FIG. 1. The user interface preferred for use by the care provider is a graphical user interface, running for example in Microsoft Windows 98® via Microsoft Visual Basic 6.0, that interacts with the care provider as the front-end.

The front-end computer 14 is preferably a pen based computer such as the Fujitsu Model Point 1600, including a radio frequency based Proxim connection system. The use of a wireless, pen based computer allows a care provider to enter all necessary data from the point of care with minimal equipment interference. The back-end computer 12 is preferably a Hewlett Packard computer running a UNIX operating system, though any operating system compatible with the front-end computer 14 is acceptable. Both the front-end computer 14 and the back-end computer 12 are preferably Internet capable. Internet capable means each computer is connected to and may be accessed from the Internet 16. Connection to the Internet 16 is accomplished using Transfer Control Protocol/Internet Protocol (TCP/IP), and an internet service provider such as U.S. West, Iowa Network Services, or any other provider.

The front-end computer 14 is linked to the back-end computer 12 through either the Internet 16 or a direct linkage. This linkage may be either a wired or wireless linkage, such as the Proxim connection system mentioned above. Further, any other computer 18 may be connected to or accessed from either the front-end computer 14 or the back-end computer 12 through the Internet 16.

On a web page, not shown, information about healthcare related issues is presented along with an access area in which patients would be able to enter an access code and user identification so as to access and view their records and billing information. The care provider would have a separate access code and user identification which would allow the care provider to provide, edit, review, and download patient records and billing information. Should any questions arise, patients are able to click on the e-mail address provided to ask a care provider to address their concerns. The web page is preferably created in hyper text markup language (HTML).

To provide patient records and billing information over the Internet 16 requires a high level of security in order to ensure no access is given to non-patients. This form of Internet security can be provided for by implementing the measures as stated in U.S. Pat. No. 5,898,830 to Wesinger, Jr., et al., hereby incorporated by reference. Of course, the front-end computer 14 may also be Internet capable.

Figure 2A:
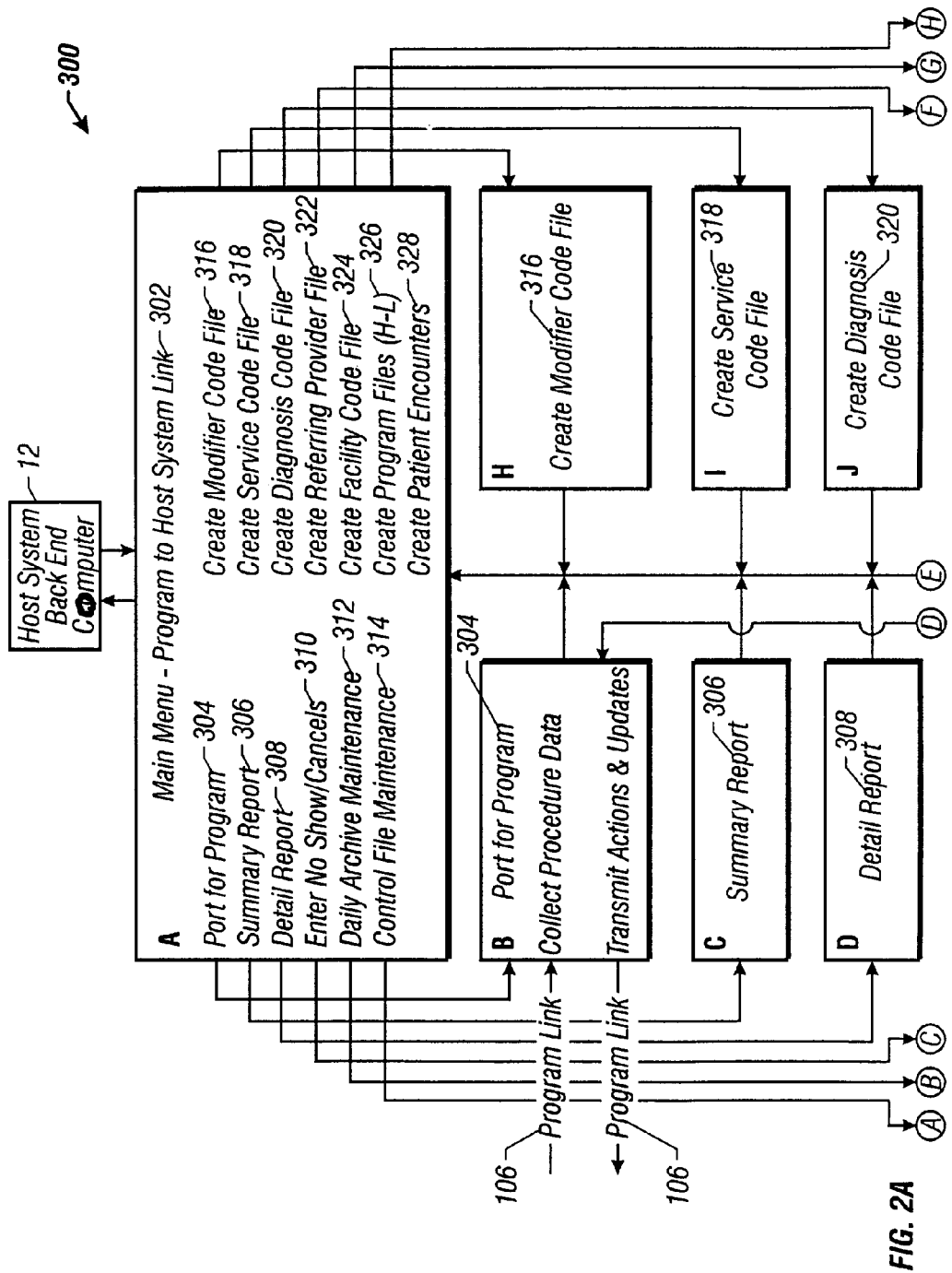
FIGS. 2A and 2B (collectively referred to as "FIG. 2") are a flow chart of the back-end of the present invention.
Figure 2B:
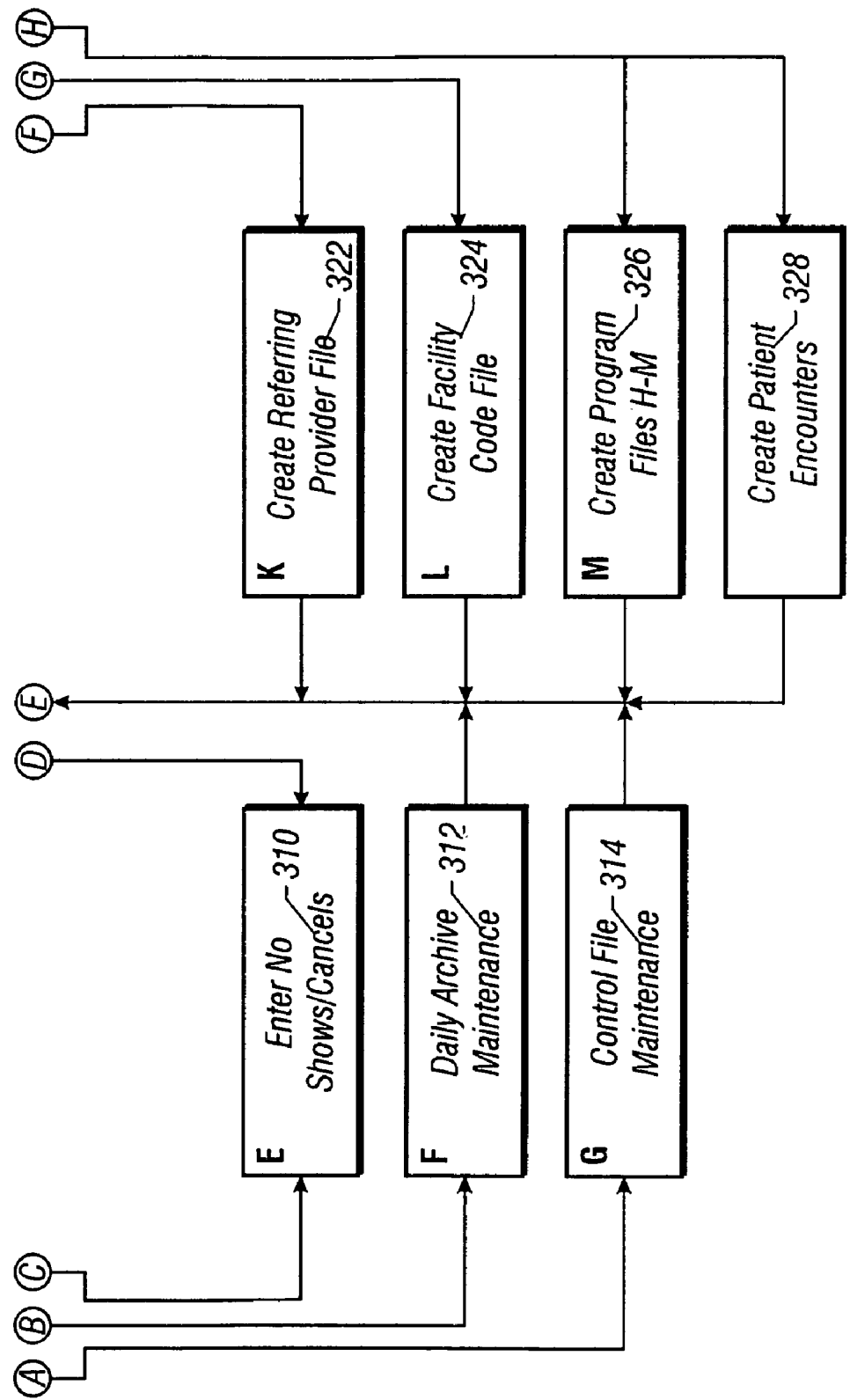
Figure 3A:
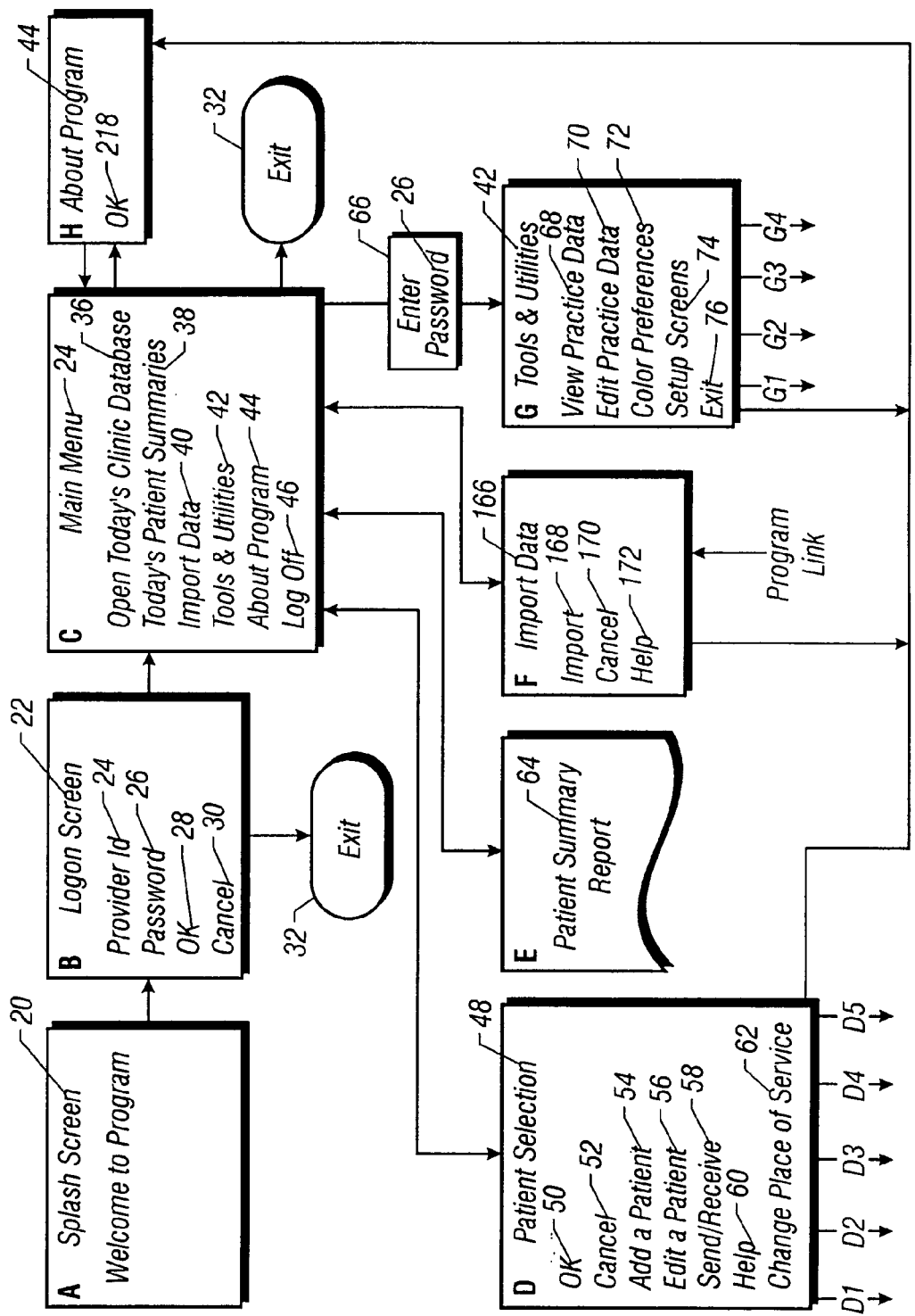
FIGS. 3A, 3B, 3C, and 3D (collectively referred to as "FIG. 3") are a flow chart of the front-end of the present invention.
Figure 3B:
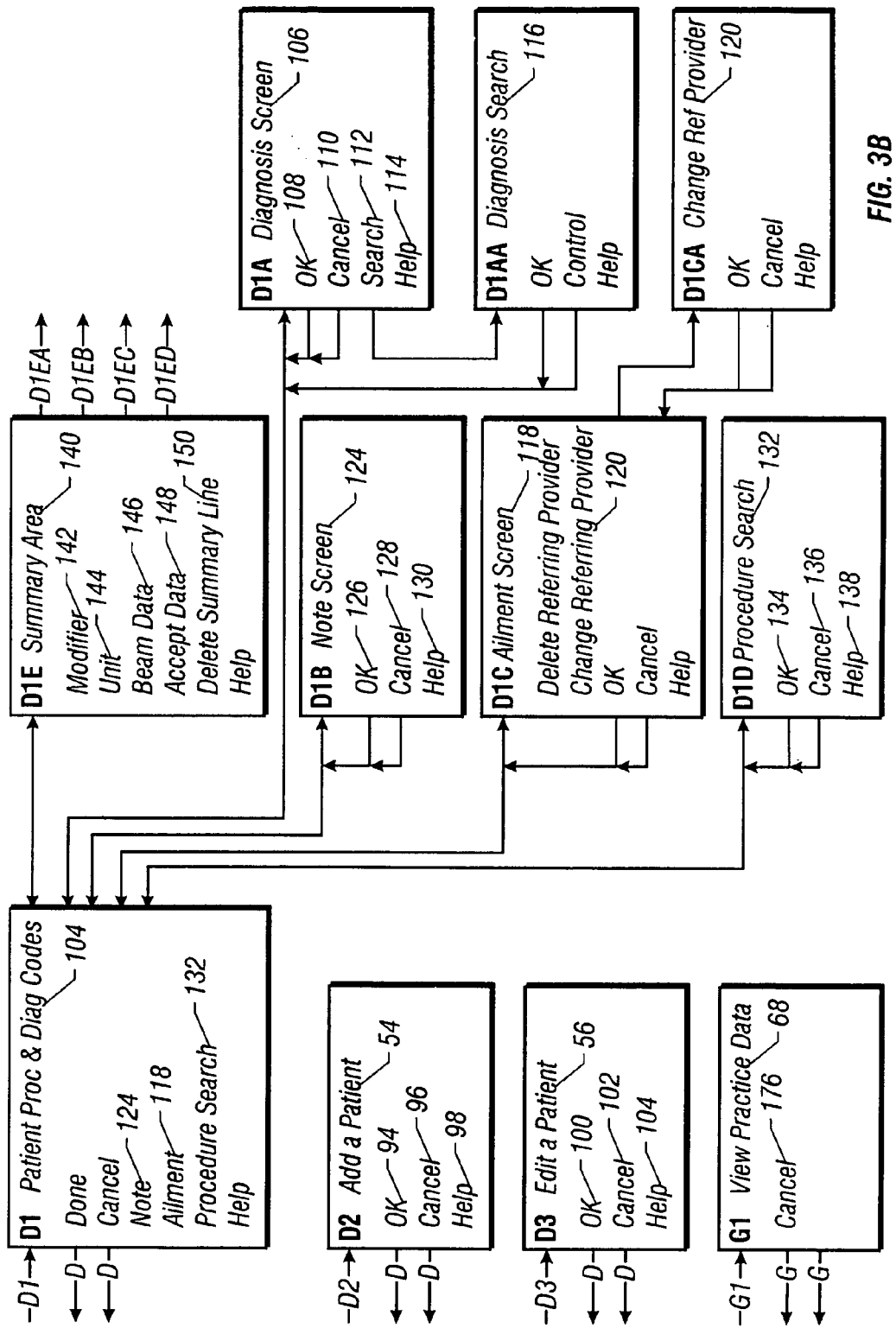
Figure 3C:
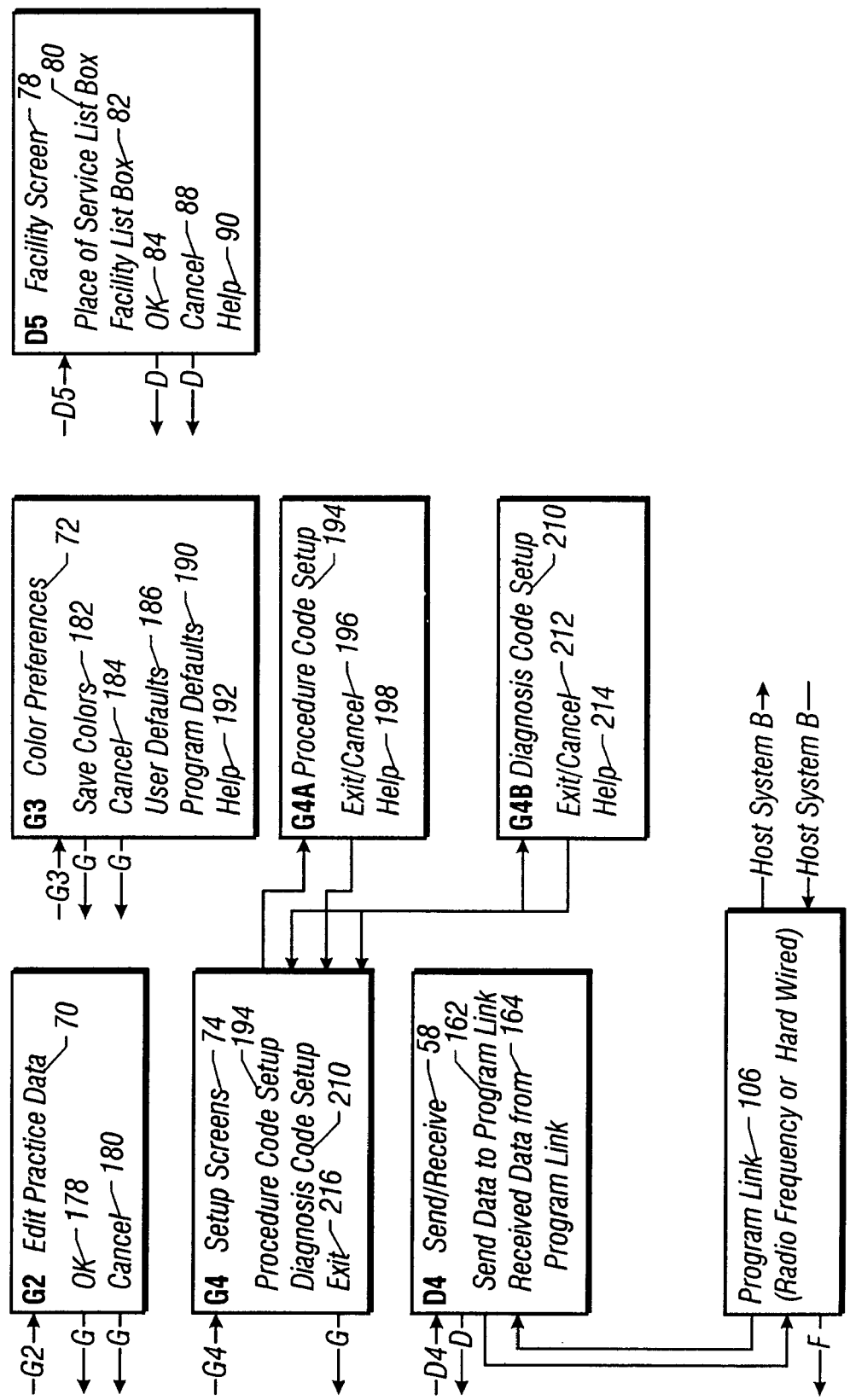
Figure 3D:
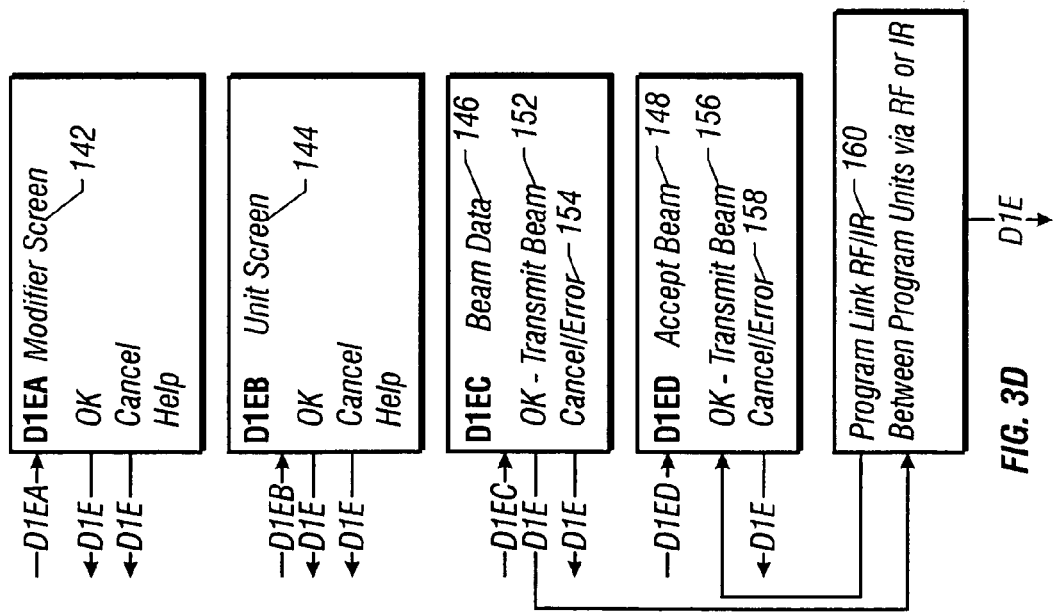

As shown in FIG. 2, a linking computer program 300 is located on the back-end computer 12. The linking computer program 300 uses a patient database to create a patient work file on the back-end computer 12. The patient work file is a text file which contains a list of all patients, and their necessary accompanying records, to be seen for a specific day such as the current day.

The linking computer program 300 initially presents the care provider, system administrator, or user, with a main menu 302. The main menu 302 screen, presents the care provider with several options, including a port for program option 304, a summary report option 306, a detail report option 308, a enter no shows/cancels option 310, a daily archive maintenance option 312, a control file maintenance option 314, a create modifier code file option 316, a create service code file option 318, a create diagnosis code file option 320, a create referring provider file option 322, a create facility code file option 324, a create patient encounters option 328 and a create program files option 326.

The control file maintenance option 314 governs information regarding the front-end program described below and its interaction with the back-end computer 12. The control file maintenance option 314 segregates the location of the front-end program data files, in relationship to the back-end system.

A reference database may be maintained on the back-end computer 12 or any other system 18 to which the back-end computer 12 may connect either through hard wire linkage or wireless linkage. The reference database may be accessed from or over the Internet 16. The reference data base contains all procedure codes, modifier codes and diagnosis codes needed, as well as a complete patient/client list. The present invention uses and obtains the latest electronic versions of the American Medical Associations CPT as well as International Classification of Disease $9^{th}$ Edition (ICD-9CM) terminology. These codes may be downloaded from the Internet 16 or from disks. Additionally, if necessary, these codes may be input by a system administrator.

Using the reference database, the create modifier code files option 316 creates the modifier code file for export to the front-end computer 14 containing all modifier codes residing on the back-end system. Again using the reference database, the create service code file option 318 creates a file for export to the front-end computer 14 containing all procedure or service codes, residing on the back-end system. Using the reference database again, the create diagnosis code file option 320 creates a file for export to the front-end computer 14 containing new or updated diagnosis codes.

The create referring provider file option 322 creates a file for export to the front-end computer 14 containing all referring provider information and codes, residing on the back-end system. The create facility code file 324 creates a file for export to the front-end computer 14 containing all current facility information residing on the back-end system.

The create program code file option 326 creates a file for export to the front-end computer 14 containing all of the current information listed above for transmission in batch mode. The use of create program code file option 326 alleviates the need to run each option separately.

The create patient encounters option 328 creates a patient work file which contains all of the patients with their corresponding appointment times for the current day. The patient work file created by the patient encounters option incorporates the current information compiled by the create program code file option 326 or any of the separately run options. The current information is incorporated with each patient's information such that should the care provider choose, the care provider may select only one patient at a time and still be presented with all of the current information at the time of the patient's appointment.

The daily archive maintenance option 312 moves the contents of the patient work file to a file entitled using the work file name as the prefix and the current day's date as the suffix. The daily archive maintenance option 312 clears out and stores the previous day's work file.

The summary report option 306 provides the care provider with a summary report of general data regarding the procedure charges which may be viewed and/or printed. The detail report option 306 provides the care provider with a printed detailed report regarding the procedure charges with related diagnosis codes for the day which may be viewed and printed.

The enter no shows/cancels option 310 updates the patient work file for those patients that have not shown up for their appointments or have canceled their appointments. The updated work file is then transmitted to the front-end computer 14 via the program link 106 described below, or transmitted from the front-end system to the back-end system via the program link.

The port for program option 304 opens the program link 106 described below. All files, including either the batch file created by the create program code file option 326 or the individual files by the create options above, the updated or current patient work file are transmitted to the front-end computer 14 via the program link 106 as described below.

Further, the back-end computer 12 contains a billing program capable of receiving individual patient data and forming a Health Care Financing Administration (HCFA) Form 1500 statement for billing based on services performed and treatments given as shown in the patient work file. Using the appropriate information from the patient work file including the codes representing the services performed, the billing program determines the proper amount of charges due for services rendered on each particular visit for each particular patient. Additionally, the billing program may be adapted to transfer patient data from the patient work file to electronic versions of other insurance and governmental forms.

The core of the billing and records keeping system 10 of the present invention is a computer program which makes it possible to place all the responsibility for billing and record keeping on the care provider while ensuring the care provider has the latest up-to-date codes available from the back-end computer 12 as described above. The graphical user interface and object-logic tiers of the present invention are programmed for a front-end computer, preferably the Fujitsu Model 1600 running on a Microsoft Windows 98® platform. The preferred programming languages are Microsoft Visual Basic and C++.

FIG. 3 shows a flowchart of a computer program which resides on the front-end computer 14 of FIG. 1. The computer program is capable of communicating with the back-end computer 12, and is therefore designed for use over networks or the Internet. Communication preferably takes place over a Proxim radio frequency based system, but may also use hard wired connections, such as telephone lines or Ethernet lines, or a radio frequency modem and accompanying antenna and system. The back-end computer 12 may be a single computer or other system, including existing hospital information support systems, or remote Internet access servers.

Figure 4:
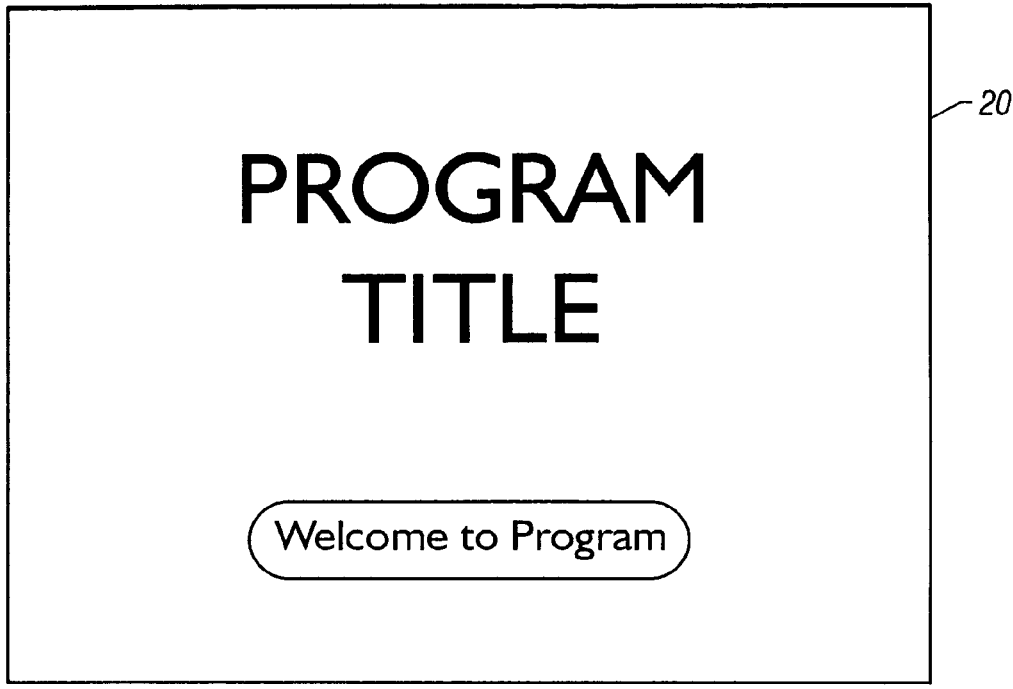
FIG. 4 is a pictorial representation of the Splash screen.
Figure 5:
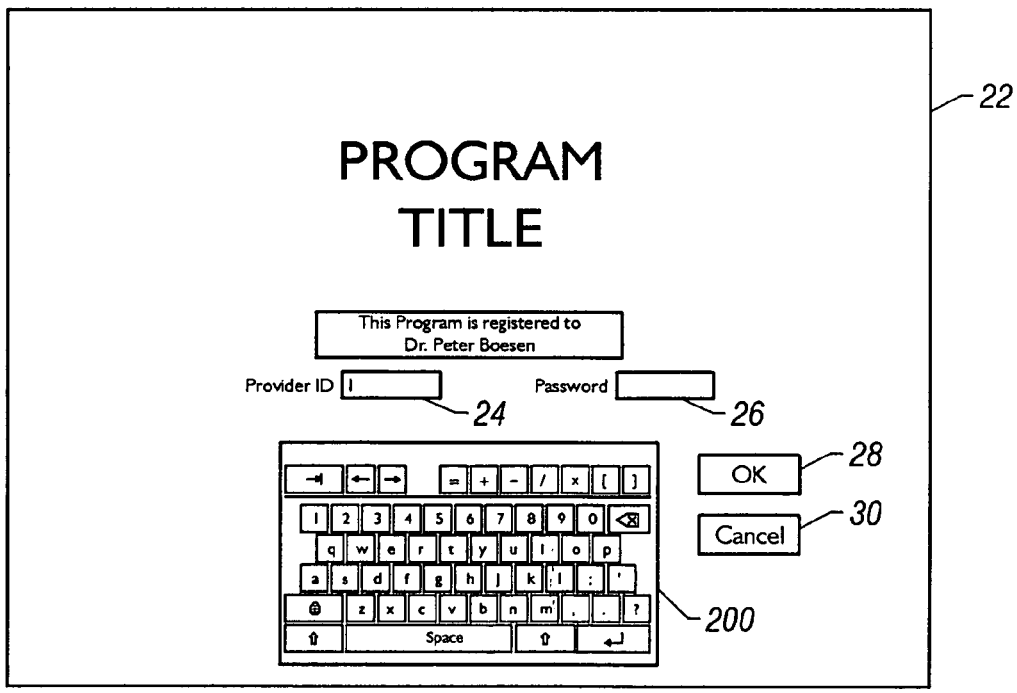
FIG. 5 is a pictorial representation of the Log On screen.

As shown in FIG. 3, upon start up, a care provider is presented with a splash screen 20, shown in FIG. 4, which welcomes the care provider to the system 10 and gives general information regarding the software licensing and title. After this brief welcome, the logon screen 22, shown in FIG. 5, appears. The logon screen 22 requires the care provider to enter a proper user identification 24 and password 26 in the appropriate text fields shown in FIG. 5, and select the OK option 28 push button. At initial startup, a general user identification 24 and password 26 may be used. As is further shown in FIG. 5, an on-screen keyboard 200 may be used to enter in the identification 24 and password 26. The on-screen keyboard is integral to the screen and remains screen specific. Additionally, software capable of recognizing handwriting may be installed onto the front-end computer 14 allowing the care provider to simply write the identification 24 and password 26 into the appropriate text fields via pen input.

The identification 24 and password 26 may be changed to a care provider specified identification 24 and password 26 through the Edit Practice Data Screen of the Tools and Utilities Sub Menu, shown in FIG. 6, as discussed further below. This ensures patient data will only be accessed by authorized personnel, further ensuring patient record privacy. Should the care provider fail to enter a proper identification 24 and password 26 or choose to cancel the logon operation by selecting the cancel option 30, such care provider will be directed to the exit 32 of the computer program.

Figure 7:
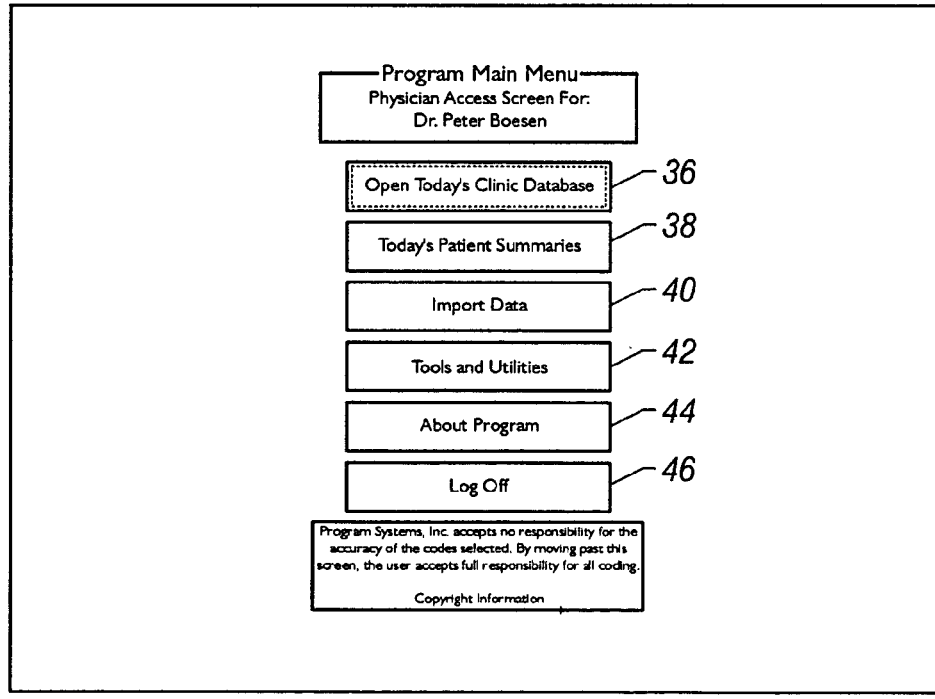
FIG. 7 is a pictorial representation of the Main Menu screen.

Once access has been obtained, the main menu 34 of the computer program is displayed as shown in FIG. 7. The main menu 34 of the computer program consists of a screen which presents the care provider with several options. From the main menu 34, the care provider may choose an option, by simply pressing the pen of the pen based computer on the appropriate push button on the screen representing that option. The options available on the main menu 34 include an option for opening today's clinic database 36, an option for evaluating patient summaries 38, an option to import data 40 from the back-end computer 12, a tools and utilities option 42, an option to evaluate the program source data 44, and a log off option 46.

As shown in FIG. 8, upon pressing the push button for the option for opening today's clinic database 36, the patient selection screen 48 is displayed, showing a list of the current day's patients compiled from the transmitted patient work file discussed above, with the first patient highlighted in the patient list box 49 along with the current place of service for that patient. Along with the name of the patient, the patient's date of birth, provider, encounter number, the date of current encounter, the time for the appointment, the back system account number, the action status and the result of actions taken status is displayed.

The patient selection screen 48 allows the care provider to select which patient is being cared for. Selection is accomplished by pushing on the patient name with the pen and thereby highlighting the patient. Once the correct patient has been highlighted, the OK option 50 push button is selected. If the care provider no longer wishes to select any patient, the care provider may return to the main menu 34 by selecting the cancel option 52 push button.

The patient selection screen 48 further allows the care provider to edit the location at which services are performed by selecting the change place of service option 62 push button. Selecting the change place of service option 62 directs the care provider to the Facility Selection screen 78, as shown in FIG. 9. The Facility Selection screen 78 displays a place of service box 80 and a facility list box 82. By highlighting the place of service and the facility of service, no facility selection need be made for the care provider's office, and then selecting the OK option 84 push button, the care provider can change the place of service. Clicking the cancel option 88 push button will keep the current place of service information. A help option 90 push button can be selected and will display helpful information on the screen. Selection of the place of service allows the care provider to quickly indicate whether services are to be performed as an in-patient, out-patient, clinic or other service.

Figure 10:
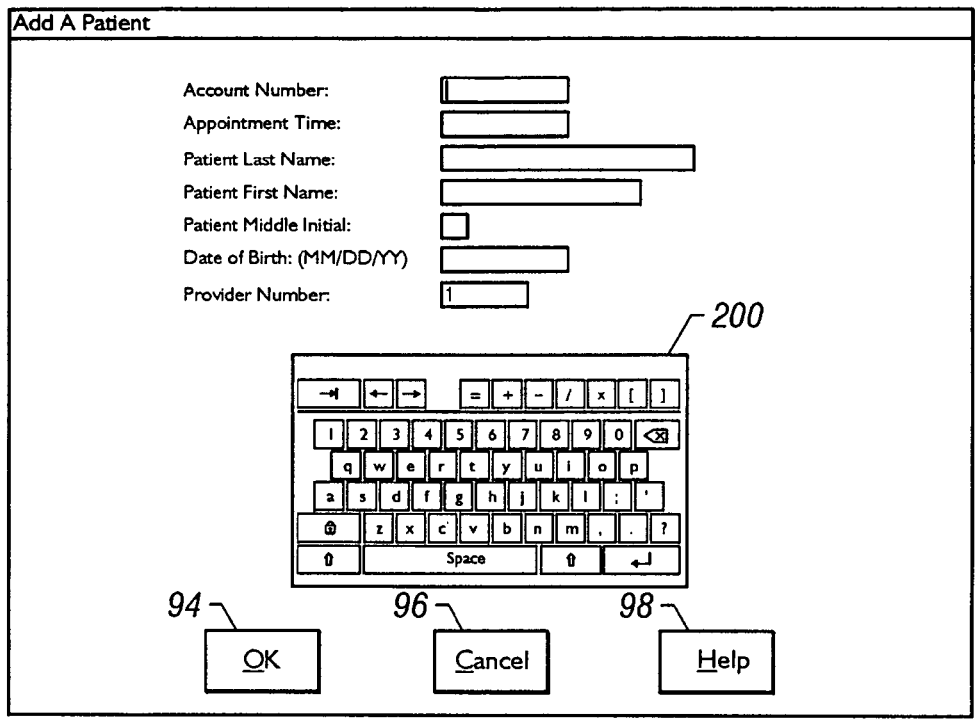
FIG. 10 is a pictorial representation of the Add A Patient screen.
Figure 11:
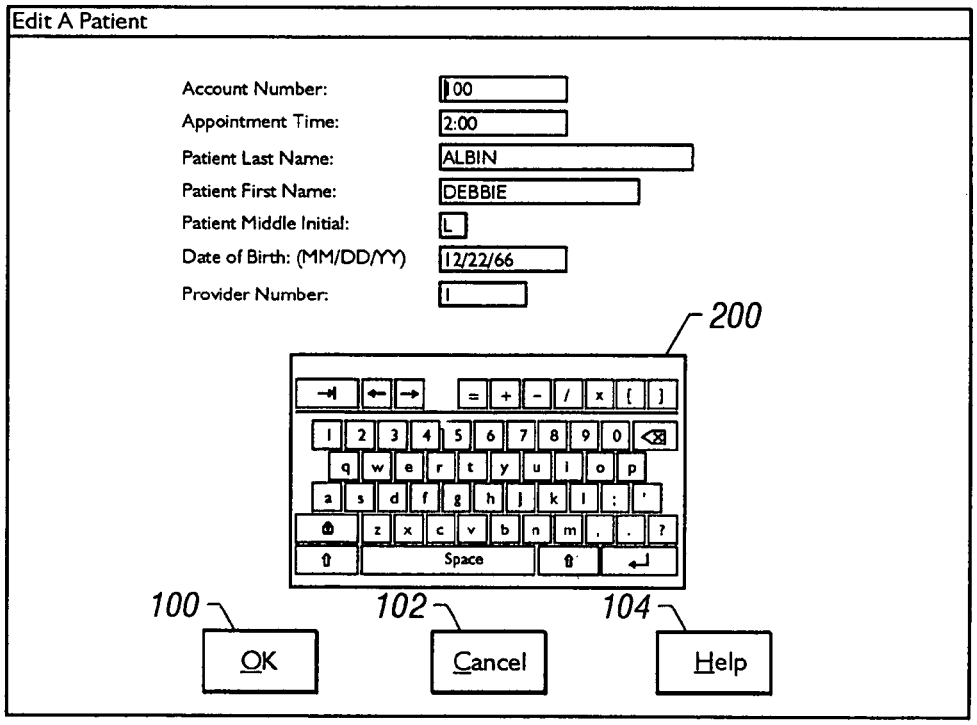
FIG. 11 is a pictorial representation of the Edit A Patient screen.

As shown, the select a patient screen of FIG. 8 further allows the care provider to add, as shown in FIG. 10, or edit, as shown in FIG. 11, individual patient data. Therefore, the responsibility for patient record keeping falls on the care provider rather than a non-care providing person who must interpret the care provider's notes and/or dictation to arrive at the data in question.

The care provider may add patient profiles for the current day's processing. From the patient selection screen, shown in FIG. 8, the care provider can select the add a patient option 54. This directs the care provider to the add a patient option 54 screen, as shown in FIG. 10.

The add a patient option 54 screen includes several text boxes which allow the care provider to input data concerning the patient, including the account number, the appointment time, the patient's last name, the patient's first name, the patient's middle initial, the patient's date of birth, and the care provider's provider number. Other information can be added by adding additional text boxes and customizing the add a patient option 54 screen to include desired information relevant to the type of services provided.

Here again the care provider may use the on-screen keyboard 200 or the pen input to add an individual patient profile. Selecting the OK option 94 push button enters the patient information. Upon selecting the OK option 94, the patient profile is immediately available for use with the rest of the billing and records system 10. Selecting the cancel option 96 push button will return the care provider to the select a patient screen 48. Additionally, a help option 98 push button is provided to provide helpful information to the care provider upon request.

Similar to the add a patient option 54 is the edit a patient option 56. Unlike the add a patient option 54, the edit a patient option 56 screen, shown in FIG. 11, presents the care provider with text boxes already completed with patient information of the highlighted patient to be edited. This patient information may be edited through the use of either the pen or the on-screen keyboard 200. The OK option 100, the cancel option 102, and the help option 104 push buttons work similar to those in the add a patient option 54.

The patient selection screen 48 also includes a send/receive option 58. After a patient has been cared for, the patient data is ported to the back system through the program link, with a result code shown in FIG. 8 indicating successful porting to the back-end computer or an error message. The services performed action code appears on the select a patient screen 48 as an asterisk in the action column of the patient list before sending the data to the back-end system. Once the updated patient data has been sent, an "S" is shown in the Action Section. Once data has been received by the back-end system 12, the back-end system 12 transmits data to the front-end system 14 indicating the latest data has been received, indicating the result of successful transmission of code data with an "x" in the result column and, thereby changing the action code to an "S" as shown in FIG. 8.

The send/receive option 58 screen uses the program link 106 to send and receive patient or coding data between a front-end computer 14 and a back-end computer 12. Simultaneously, all patient data with an asterisk action code is transmitted. This allows for single batch or multiple batch transfer of patient data capabilities. By selecting the receive data option 164, data for new patients to be seen, cancellations, no shows, updates, or similar information is transmitted from the back-end computer 12 to the front-end computer 14 with each activation of the Send/Receive link. This capability to send and receive individual patient data allows the care provider to properly bill a patient upon the patient's departure from the care provider's office and is responsive to the burdens placed upon the typical operations of a clinic, namely add-on patients, such as "walk-ins" or "work-ins."

All transmission between the front-end computer 14 and the back-end computer 12 or vice-versa occur via the program link 106 as described below. Such importing/exporting of data may take place immediately, updating the care provider while viewing the patient selection screen 32.

The patient selection screen 48 further allows the care provider to ask for help by selecting the help option 60 push button. Help is provided in all of its applications in the present invention internally, via the front-end computer 14, or the Internet 16 to which the front-end computer 14 are connected. Help is routed through the program link 106 if necessary.

Preferably, the front-end computer 14 and back-end computer 12 are linked wirelessly via the program link 106. The program link 106 is preferably a wireless linkage using a radio frequency (RF) local area network (LAN) such as Proxim or BreezeCom. Other forms of communication between the front-end computer 14 and the back-end computer 12 may be used such as cellular, time modulated ultra wide band radio frequency, infrared, or any type of conventional hard wiring which is commonly known in the art.

Figures 12, 13:
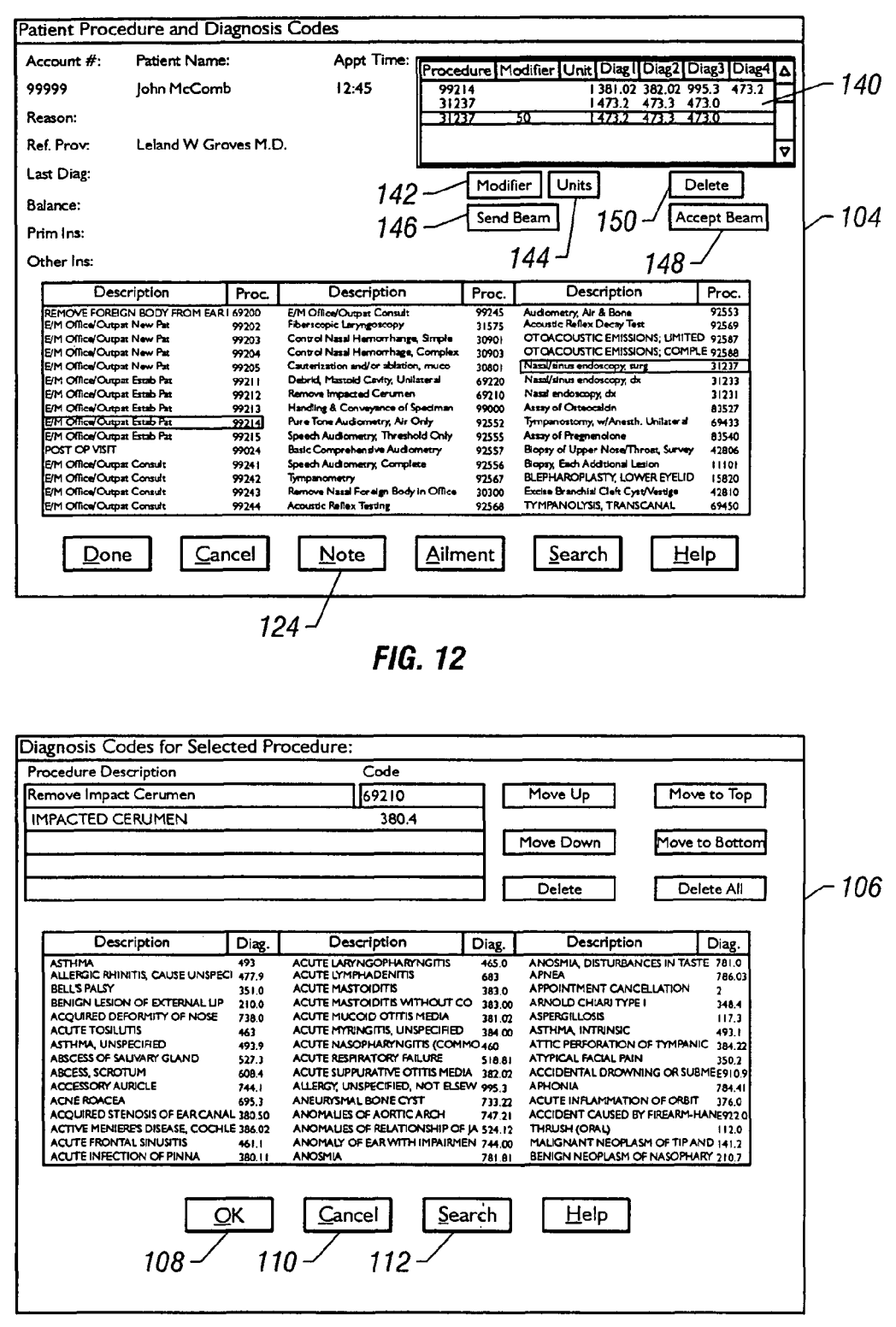

Once a patient has been selected from the patient selection screen 48, the care provider is directed towards the Patient Procedure and Diagnosis Codes 104 screen as shown in FIG. 12. From here, the care provider can select the proper procedure and diagnosis codes from the American Medical Associations CPT. The patient procedures codes and a description of the procedure appear at the bottom of the screen shown in FIG. 12. Upon selecting the appropriate procedure code, the care provider is directed to the diagnosis screen 106 as shown in FIG. 13.

Figure 14:
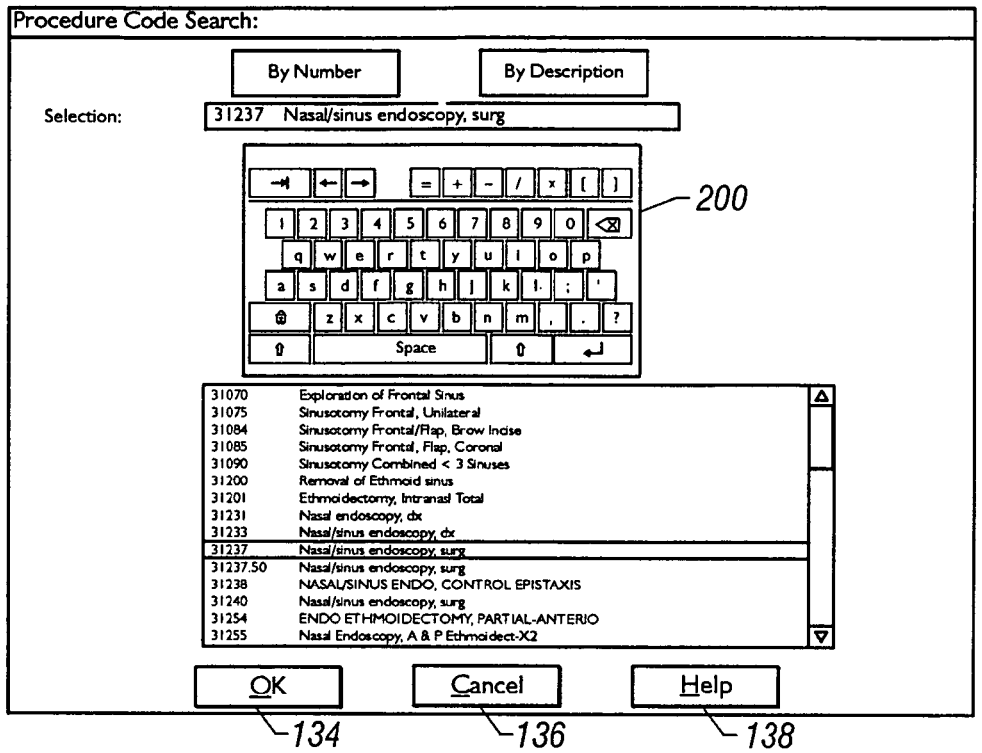
FIG. 14 is a pictorial representation of the Procedure Search Option screen.

If the proper procedure code is not shown, the care provider may select the procedure search option 132. Clicking on the procedure search option 132 push button directs the care provider to the procedure search option 132 screen as shown in FIG. 14. Here the care provider can search by number or by description for the procedures not previously found using either the pen or the on-screen keyboard 200. Selecting the OK option 134, or the cancel option 136 returns the care provider back to the patient procedures and diagnosis codes screen 104 with or without the selected codes respectively. The care provider may also select a help option 138 which will present the care provider with helpful information.

In the diagnosis screen 106, the care provider can select the proper diagnosis code(s). Up to four diagnosis codes can be selected, however, if more are required by the Health Care Financing Administration (HCFA) in the future, this number can easily be expanded. The selected diagnosis code appears in the upper left corner of the diagnosis screen 106 as shown in FIG. 13 and the order of codes may be changed by highlighting the desired code and then moving the highlighted code either up or down, to the top or to the bottom by selecting the appropriate push button. Additionally, either the highlighted code or all of the codes selected may be deleted by pushing the appropriate push button. When the care provider is done selecting diagnosis codes, the OK option 108 push button is selected directing the care provider back to the Patient Procedure and Diagnosis Codes Screen 104. Additionally, if the care provider does not wish to select a diagnosis code at this time, the care provider may select the cancel option 110 push button, thereby returning the care provider to the Patient Procedure and Diagnosis Codes Screen 104. Upon pressing the cancel option push button, the care provider will be prompted to determine whether the intention to leave the screen without updating is correct. Only upon affirmation will the care provider be returned to the patient procedure and diagnosis codes screen 104, canceling the diagnosis code(s) and specific related procedure code.

Figure 15:
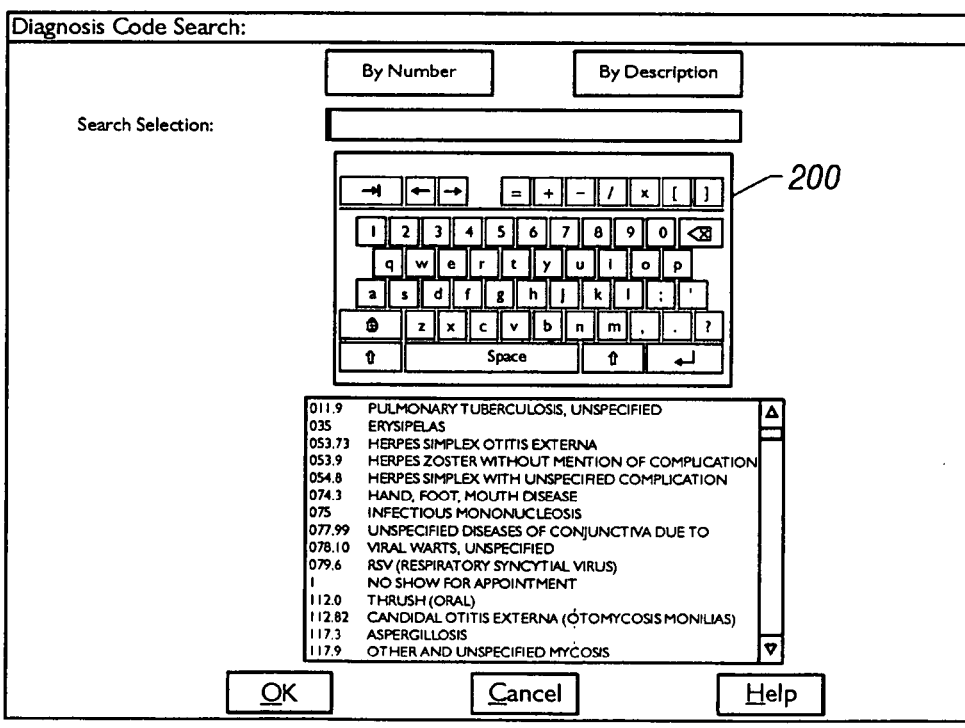
FIG. 15 is a pictorial representation of the Diagnosis Codes Search screen.

If the care provider does not see the proper diagnosis present, the care provider may select the search option 112 from the diagnosis screen 106. Selecting the search option 112 push button directs the care provider to the diagnosis search screen 116 as shown in FIG. 15. Here, the care provider may scan the vast amounts of data representing different possible diagnoses. The care provider may search by number or by description for the diagnosis codes desired. The care provider then selects the proper code using either the pen or the on-screen keyboard 200. Selecting the OK option push button returns the care provider to the patient procedure and diagnosis screen 104 with the desired input. Selecting the cancel option push button discards all input and simply returns the care provider to the procedure and diagnosis screen 104. A help push button is also provided should the care provider need assistance.

Figures 16, 17:
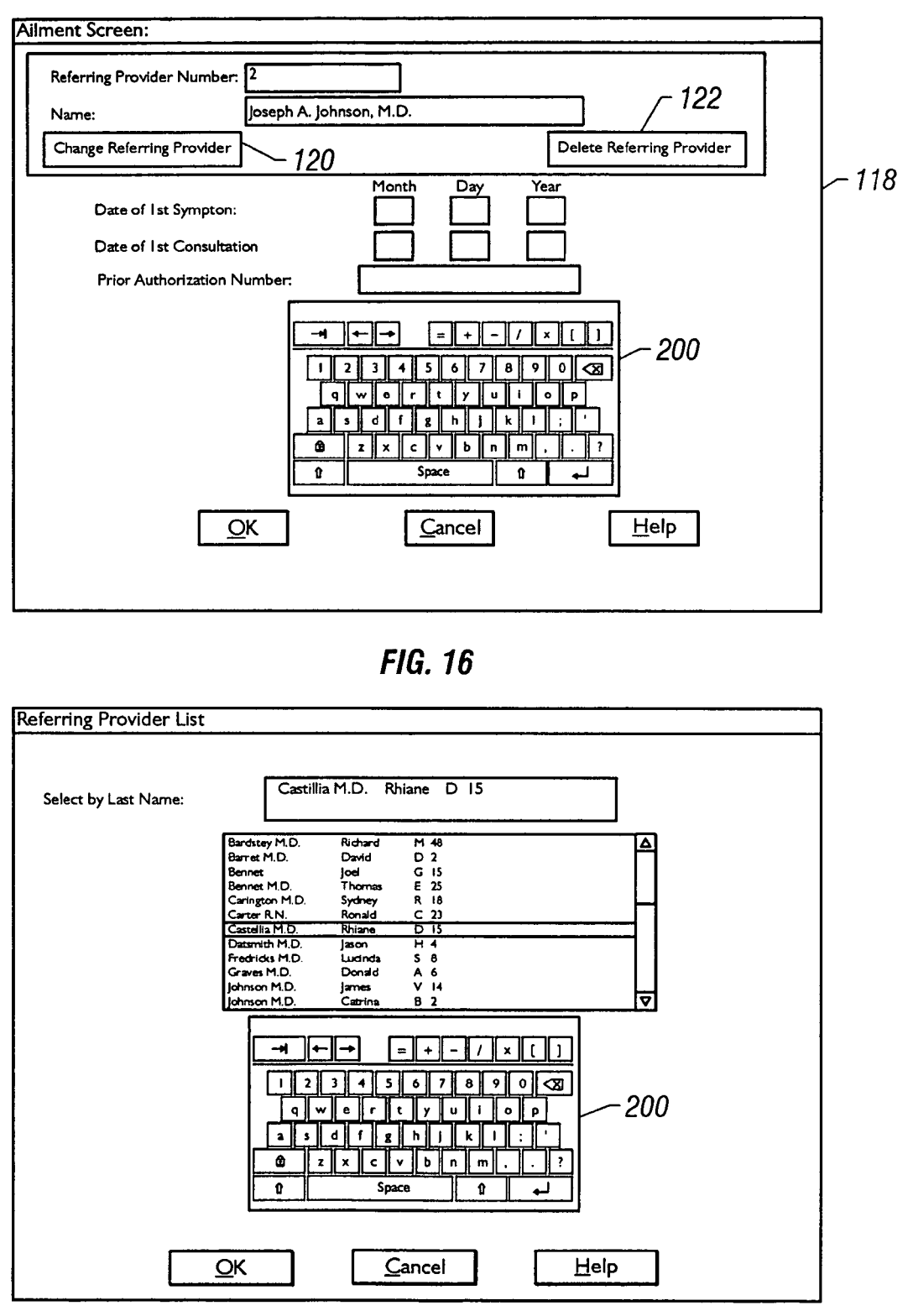

From the procedure and diagnosis screen 104, the care provider may select the ailment option. This directs the care provider to the ailment screen 118 as shown in FIG. 16. Here the ailment may be documented through the use of various text boxes labeled to show all the required fields for insurance processing including when symptoms first appeared, when the first consultation was sought, etc. The dates will default to the current day's date unless changed.

Further, the doctor who referred the patient with the respective ailment is shown including the doctor's name and referring provider number. These may be edited by using the change referring provider option 120. Upon selecting the change referring provider option 120 push button, the care provider is directed to the referring provider list screen, as shown in FIG. 17. This allows the care provider to select the referring provider from the list or type in the first letter of the name to narrow the search using the on-screen keyboard 200. Additionally, if the referring provider information is to be left blank, the care provider can delete any name listed in the text boxes by selecting the delete referring provider option 122 push button, which simply clears all text boxes relating to the referring provider. Selecting the OK option sends the care provider back to the patient procedures and diagnosis codes screen 104. A cancel option push button returns the care provider to the patient selection screen 48. Additionally, a help option push button provides help if the care provider needs assistance.

Figure 18:
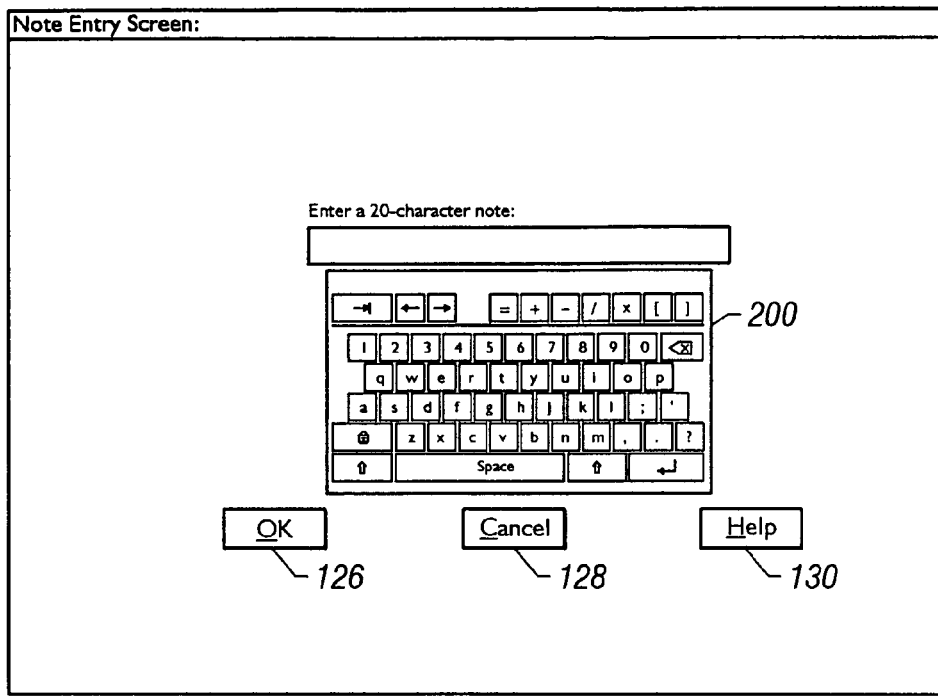
FIG. 18 is a pictorial representation of the Note screen.

The patient procedures and diagnosis codes screen 104 also includes a note option 124. By selecting this note option 124 push button, the care provider is directed to a note option 124 screen as shown in FIG. 18. Here the care provider may use the built in on-screen keyboard 200 or the pen via handwriting recognition software to enter notes for this particular patient into the text box. Again, the on screen keyboard 200 is always present on any screen where it is necessary for the care provider to enter or edit. After entering a note into the text box, the care provider may select the OK option 126, the cancel option 128, or the help option 130. Selecting either the OK option 126 or the cancel option 128 will return the care provider to the patient procedures and diagnosis codes screen 104. Selecting the help option 130 will offer help to the care provider.

Also on the patient procedures and diagnosis codes screen 104, is a summary area 140. The summary area 140 contains all procedures selected along with the modifiers, units, and diagnosis codes selected which correspond to each procedure. Selected procedures and their accompanying information may be deleted by using the delete option 150 push button. A Help button (not shown) is also provided.

Figure 19:
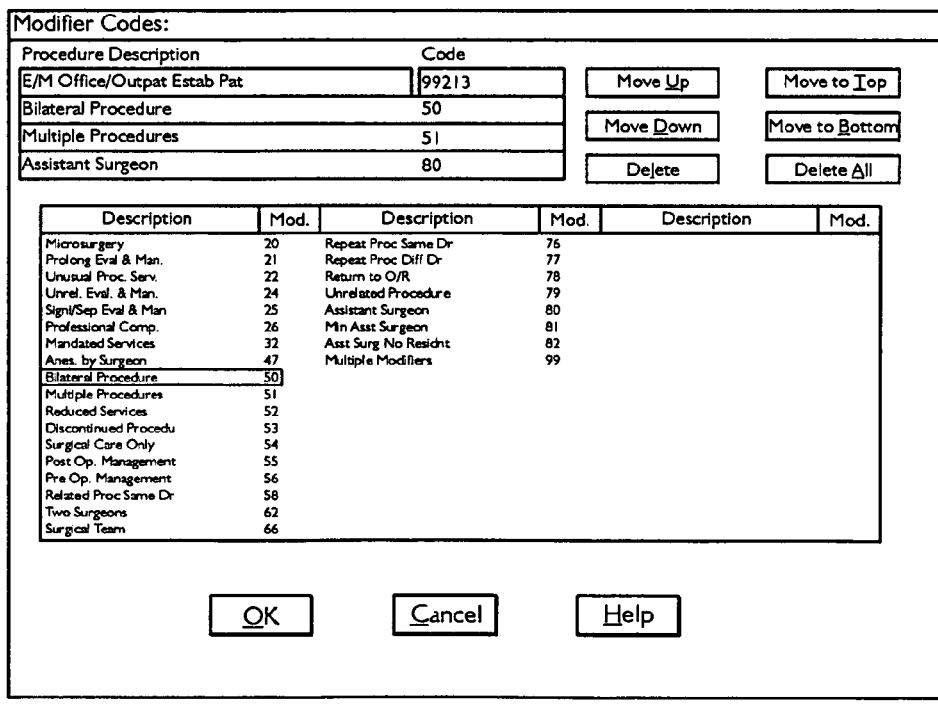
FIG. 19 is a pictorial representation of the Modifier Option screen.

Modifiers, adding further clarification to the procedures performed, may be added by clicking on the modifier option 142 push button. Upon clicking on the modifier option 142 push button, the care provider is directed to the modifier option 142 screen, as shown in FIG. 19. On the modifier option 142 screen, the care provider is presented with a list of possible modifiers relevant to the selected procedure. From this list, the care provider selects any and all necessary modifiers (up to three, as allowed by the Health Care Financing Administration). The care provider may move the selected modifier up, down, to the top or bottom using the corresponding option push buttons. Additionally, the care provider may delete either the selected modifier or all of the modifiers using the delete push button or the delete all push button respectively. Upon conclusion, the care provider clicks on the OK option push button or the cancel option push button and returns to the patient procedures and diagnosis codes screen 104 with or without the desired modifier(s) selected respectively. Further, a help option is available to the care provider in the need of assistance.

Figures 20, 21:
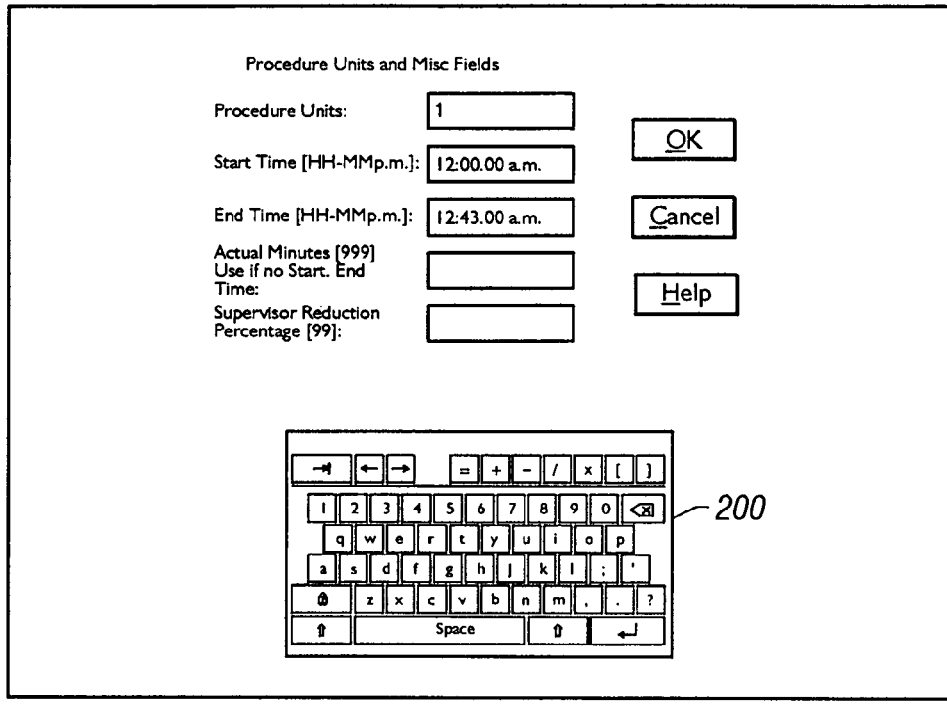
FIG. 20 is a pictorial representation of the Units Option screen.
FIG. 21 is a pictorial representation of the Summary screen.

By selecting the units option 144 and clicking on the units option 144 push button, the care provider is directed to the units option 144 screen as shown in FIG. 20. On the units option 144 screen, the care provider may enter the number of units desired in the corresponding text box. The default number of units is one. Further, the care provider may enter other information, such as the start time, end time, actual minutes, supervisor reduction percentage, etc. in corresponding text boxes through either the pen or the on-screen keyboard 200. Upon conclusion, the care provider clicks on the OK option push button or the cancel option push button and returns to the patient procedures and diagnosis codes screen 104 with or without the desired units selected respectively. Further, a help option is available to the care provider in the need of assistance.

Finally, the summary area 140 also includes a send beam option 146 and an accept beam option 148. The send beam option will transmit only the data in the summary area 140 to only another computer which is waiting for the data. Any other computer capable of accepting data is capable of receiving data from the send beam option 146 and must be "Accept beam" mode, waiting for data transmission. As only the data in the summary area 140, which includes no patient names nor identifying information will be transmitted, total patient privacy is ensured. Only another computer which is specifically waiting for data regarding a particular patient will be able to make use of the data. This situation occurs often between doctors who must rely on the work done just previously by another care provider. To comply with insurance and governmental regulations, doctors must include all coding for all prior procedures performed on a particular patient.

In order to be waiting for data from another computer, or if another computer is transmitting the data, the front-end computer 14 of the present invention, must click on the accept beam option 148. This allows the front-end computer 14 to receive data from another front-end computer using a non similar back-end link system. Should an error occur, an error message appears indicating the error.

Both the send beam option 146 and the accept beam option 148 use a wireless linkage, such as the Proxim RangeLAN2 system. Other wireless linkage are possible, such as an Infra red laser diode system, such as currently found in the art. Further, the linkage may be hardwired to transmit data between two corresponding ports on the front-end computers 14.

If the transmission is successful, an "OK" message will appear indicating to the care provider that data has been transmitted. At any point in the process, the care provider may wish to terminate transmission and may exit the beam data option. If the transmission encounters errors, an appropriate error message is noted. Upon exiting or encountering an error message, the care provider will be passed back to the summary area 140.

From the main menu screen 34, the care provider may also view today's patient summary 38. This directs the care provider to the patient summary 64 screen which may be printed, stored, or downloaded from the back-end computer 12. The patient summary 64 screen as shown in FIG. 21, shows a list of all patients seen and processed for the current day. The list displays the account number, the patient name, the date of service, all codes that have been posted, the procedure code with modifiers and units, the first diagnosis code, the care provider number and the dollar amount of charges due per procedure performed.

Figure 22:
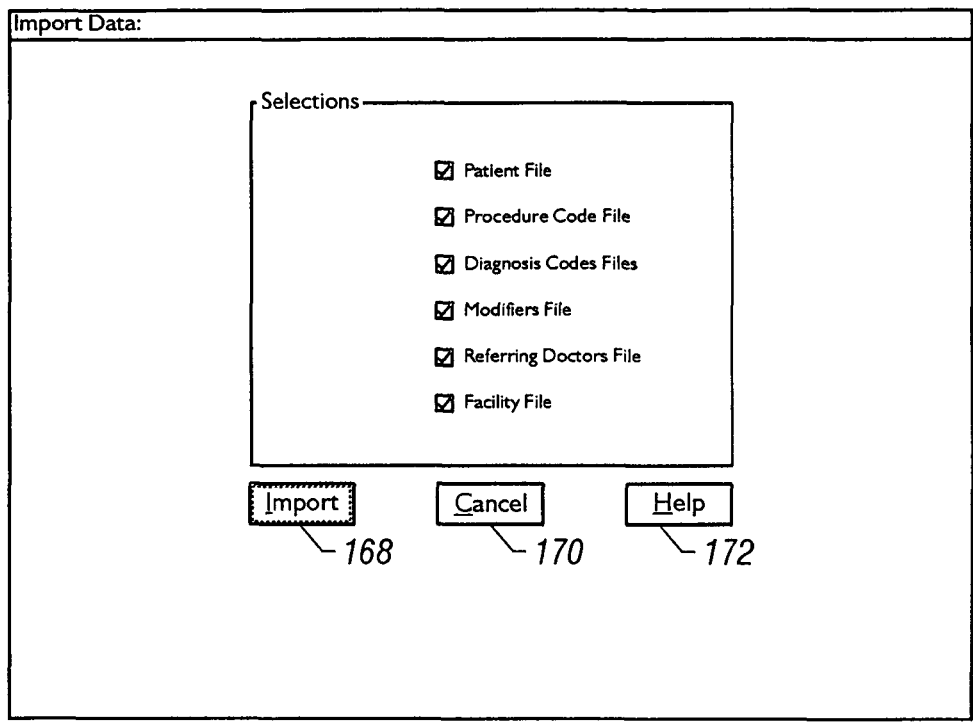
FIG. 22 is a pictorial representation of the Import Data screen.

From the main menu 34, a care provider can select the import data option 40. The care provider is directed to the import data screen 166 as shown in FIG. 22. The import data screen 166 includes several check boxes allowing the care provider to decide which files to import. The care provider may import the patient files, the procedure code files, the diagnosis codes files, the modifiers files, the referring providers files, or the facility files, or all of the above. By pressing the pen or using a mouse, the care provider may select or check the appropriate boxes. Upon pressing the import option 168 push button and using the program link 106, the care provider can import all of the desired files for the day. Only the patient files corresponding to the patients the care provider plans on seeing that day are available. Should the care provider wish to cancel the import process at any time, the care provider may click on or press the cancel option 170 push button which will cancel the operation. Should the import option 168 fail for any reason, an error message appears. The care provider is also provided with a help option 172 to provide assistance if needed.

Figure 23:
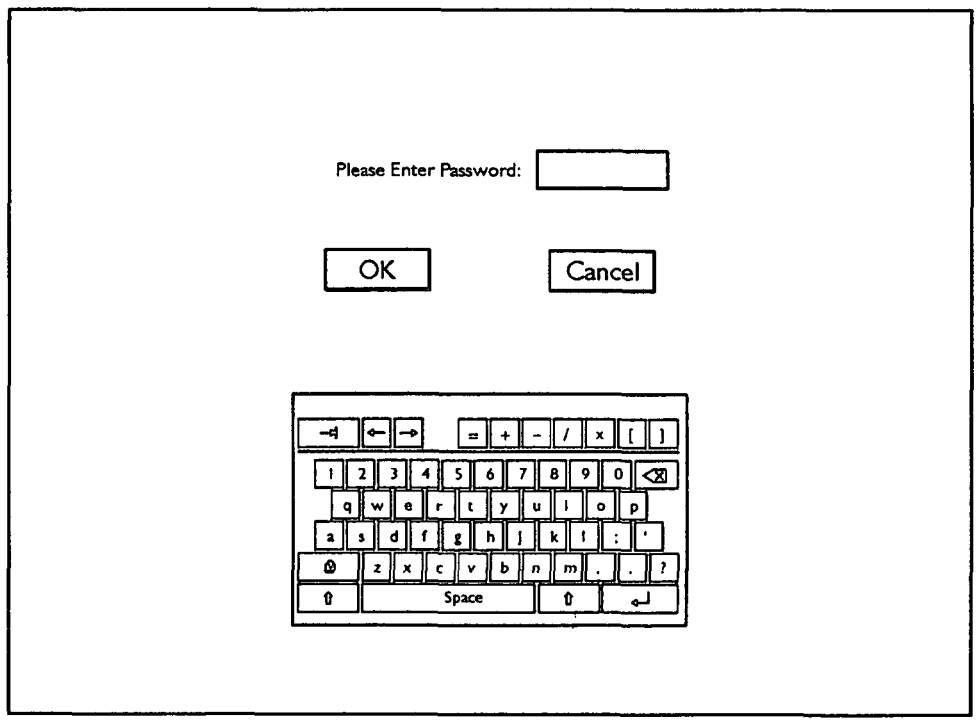
FIG. 23 is a pictorial representation of the Password Screen.
Figure 24:
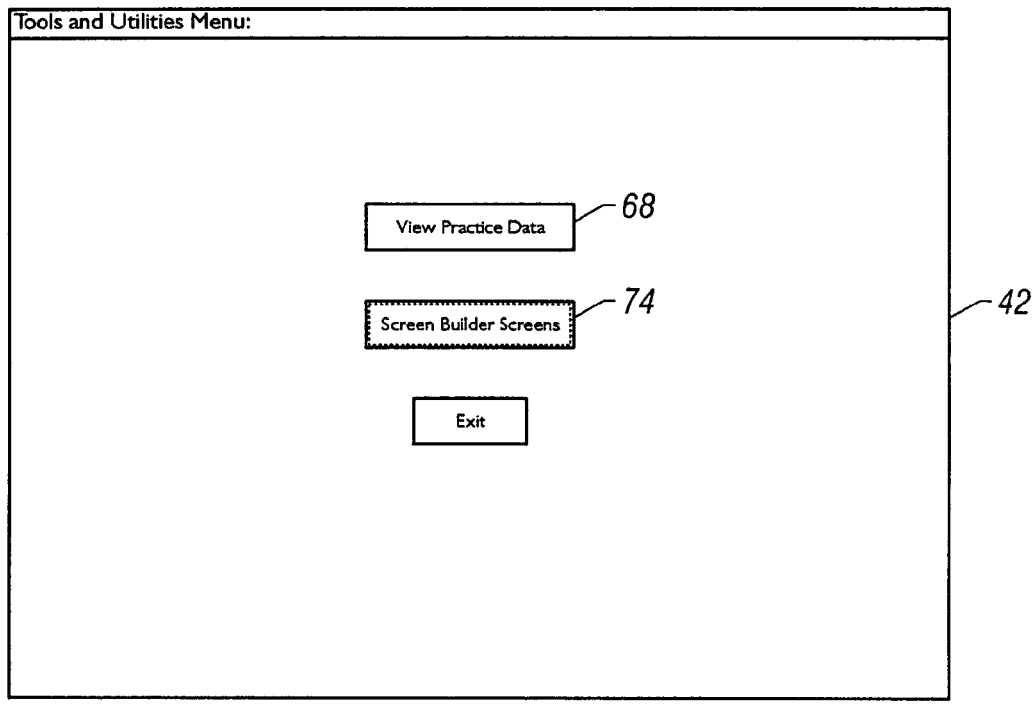
FIG. 24 is a pictorial representation of the Tools and Utilities screen.
Figure 25:
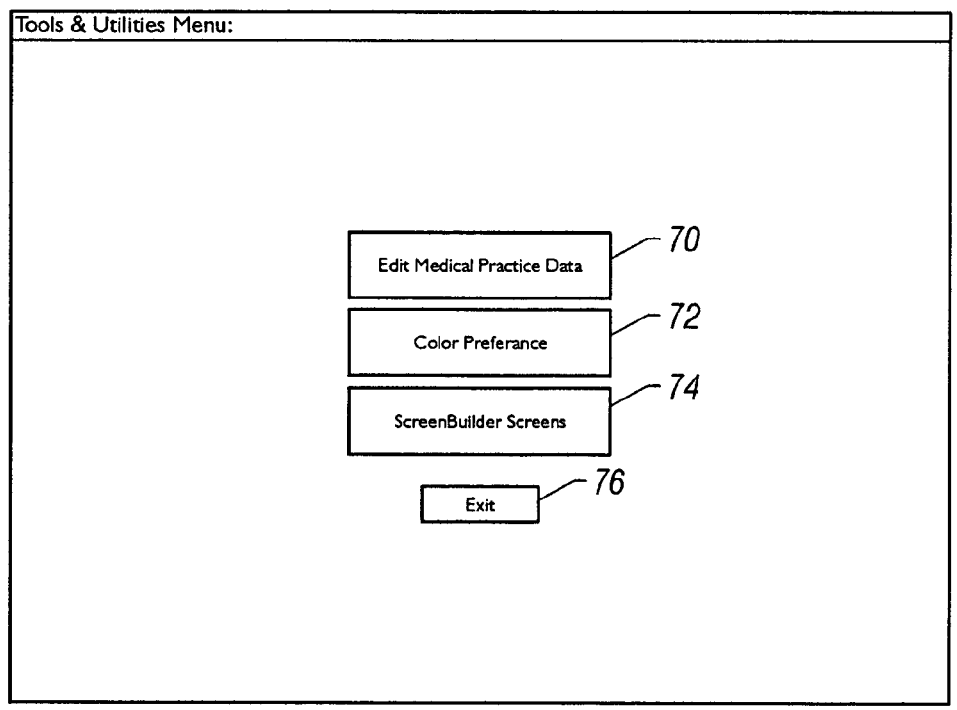
FIG. 25 is a pictorial representation of the Full Tools and Utilities screen.

The main menu screen 34 also allows the user to select the tools and utilities option 42. Upon clicking the tools and utilities option 42 push button, the user is directed to re-enter their password as shown in FIG. 23. After confirmation by the system 10, the user is directed to the tools and utilities 42 screen, as shown in FIG. 24 or a full Tools and Utilities screen FIG. 25 by entering a special password. The care provider is presented with the options to view the practice data or the set-up screen or, if password allowed, edit the practice data, select the color preferences, or enter the setup screens. One can exit with corresponding push buttons.

Figures 26, 27:
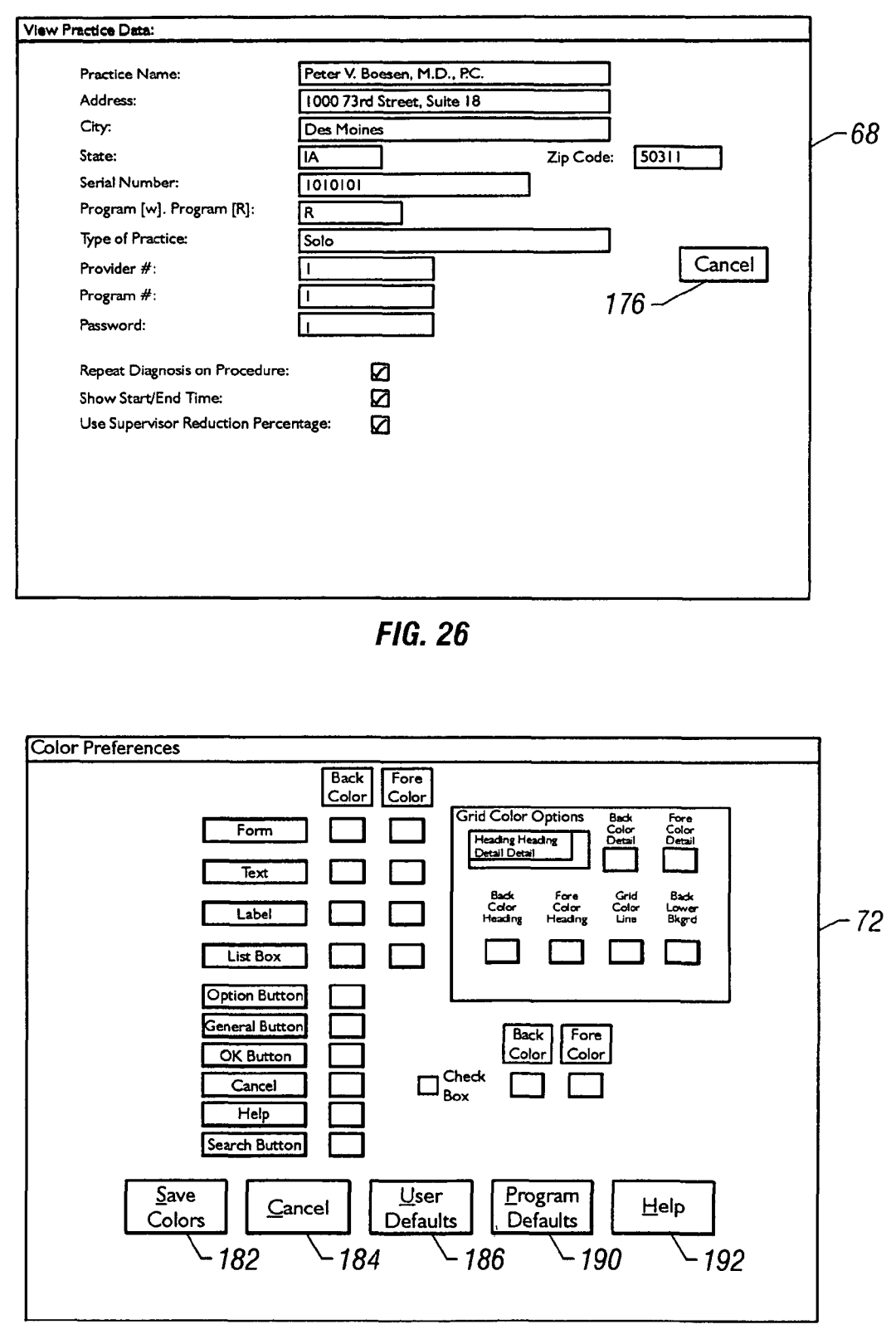

Clicking on the view practice data option 68 push button directs the care provider to the view practice data option 68 screen, as shown in FIG. 26. This presents the care provider with filled in text boxes allowing the care provider to see the practice name, address, city, state, serial number, license information, type of practice, provider number, password, identification, and view the selections made concerning various options such as repeatability of diagnosis on procedures, whether to show the start/end times and whether to use the supervisor reduction percentage. Once the care provider is done viewing the practice data, the care provider may return to the main menu by selecting the cancel option 176.

Figure 6:
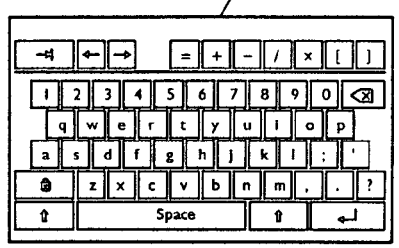
FIG. 6 is a pictorial representation of the Edit Practice Data screen.

Clicking on the edit practice data option 70 push button directs the care provider to the edit practice data option 70 screen, as shown in FIG. 6. This screen allows the care provider to change any of the information listed in the view practice data option 68 screen. After the appropriate information is entered via the keyboard 200 or the pen, the care provider selects the OK option 178. If the care provider does not want to keep any changes made, the care provider may select the cancel option 180 and return to the main menu 34.

Clicking on the color preferences option 72 directs the care provider to the color preferences option 72 screen, as shown in FIG. 27. Here the care provider may alter the colors used on the screen displays to suit the individual care provider's preferences. The color preferences may be saved by selecting the save colors option 182, or any changes may be cancelled by selecting the cancel option 184. The care provider may return to their previously established colors by selecting the user defaults option 186 or return to the pre-programmed colors by selecting the program defaults 190. Here the aesthetics of the front-end computer 14 screen may be adjusted to fit the individual care provider's preferences, fully taking into account human abilities or inabilities to differentiate between colors—e.g. red and green in red/green colorblind users. A help option 192 is also provided should the care provider need assistance.

Figure 28:
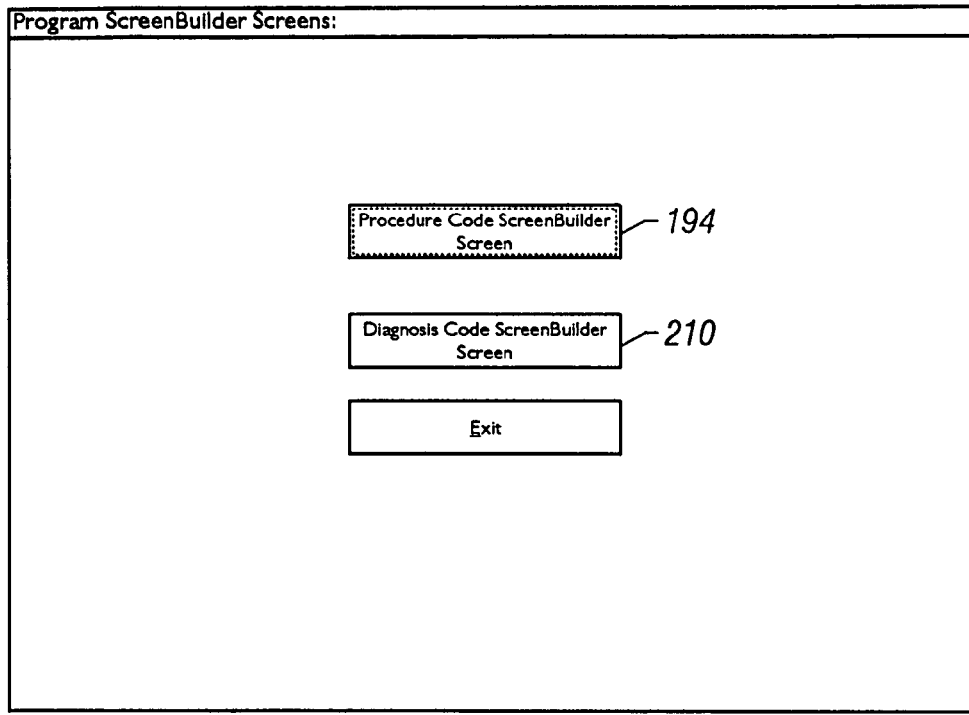
FIG. 28 is a pictorial representation of the Setup screen.

Again referring to FIG. 24, clicking on the setup screens option 74 push button directs the user to the set up screens option 74 screen, as shown in FIG. 28. Here the care provider may alter the setup of the procedure codes via the procedure code setup option 194 or the diagnosis code setup option 210.

Figure 29:
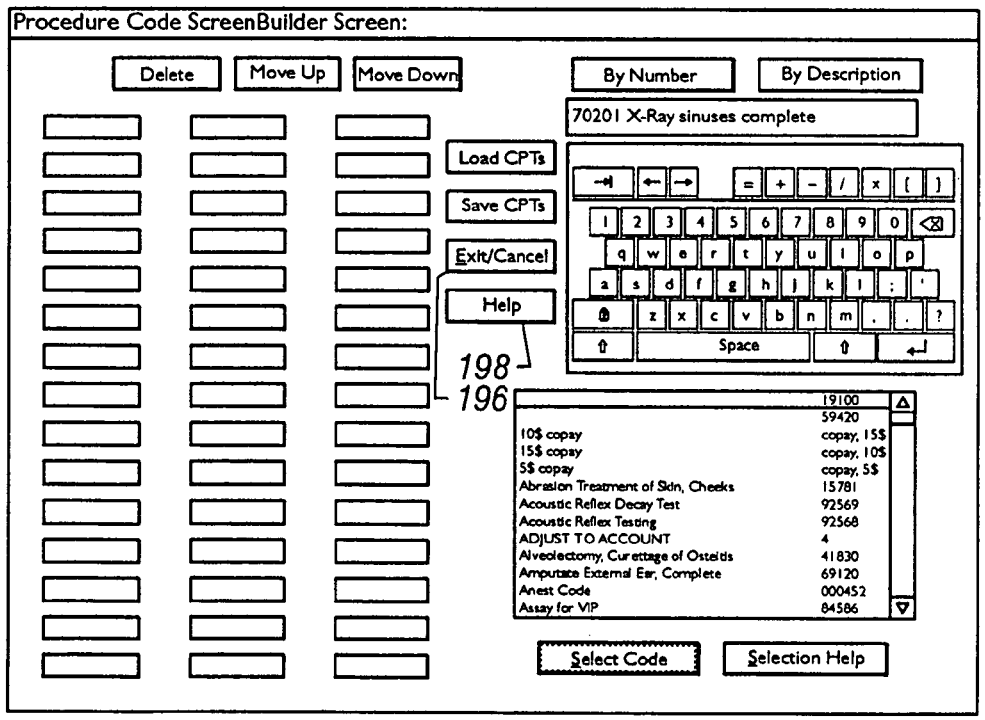
FIG. 29 is a pictorial representation of the Procedure Code Setup screen.

Clicking on the procedure code setup option 194 push button directs the care provider to the procedure code screen builder screen as shown in FIG. 29. Here, the care provider may search for codes by number or description, select the appropriate code, delete a current code, or add a new code. To import the current CPT/EM codes into the editing area, the care provider may click on the load CPTs option push button. After any and all modifications are done, the care provider can click on the save CPTs option push button. When all modifications are done the care provider may exit by clicking on the exit option 196 push button. This gives the care provider the ability to customize the procedure codes used most frequently for their individual practice. Additionally, help is available to the care provider via the help option 198.

Figure 30:
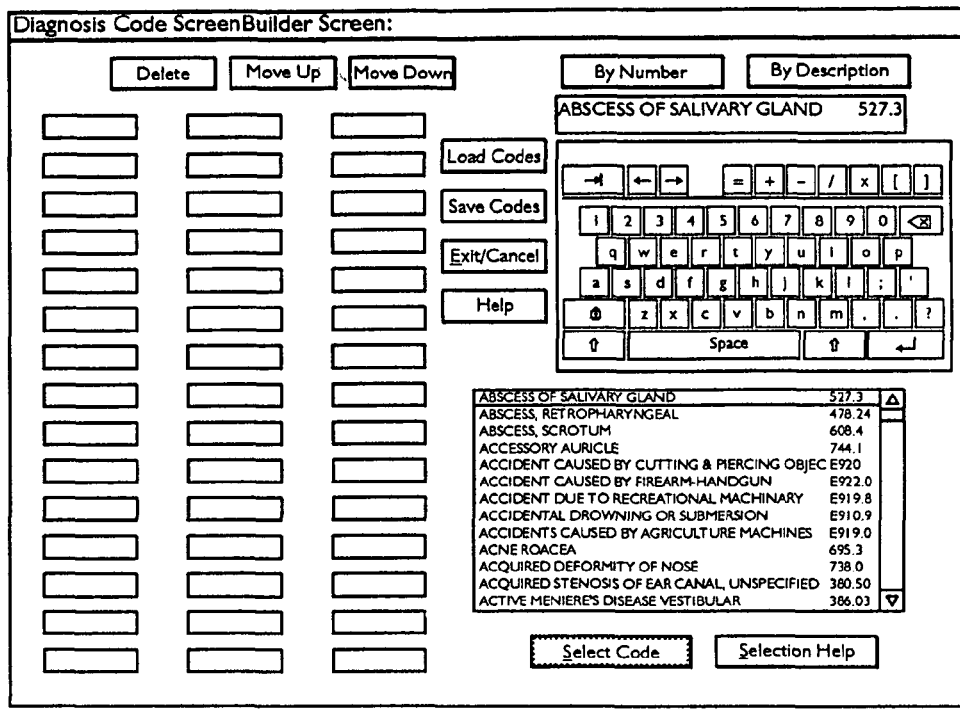
FIG. 30 is a pictorial representation of the Diagnosis Code Setup screen.

The diagnosis code setup option 210 and screen, as shown in FIG. 30, works exactly like the procedure code setup option 194, except, of course, with diagnosis codes.

Again referring to FIG. 25, the care provider may exit the tools and utilities option 42 screen by selecting the exit option 76. This returns the care provider to the main menu 34.

Figure 31:
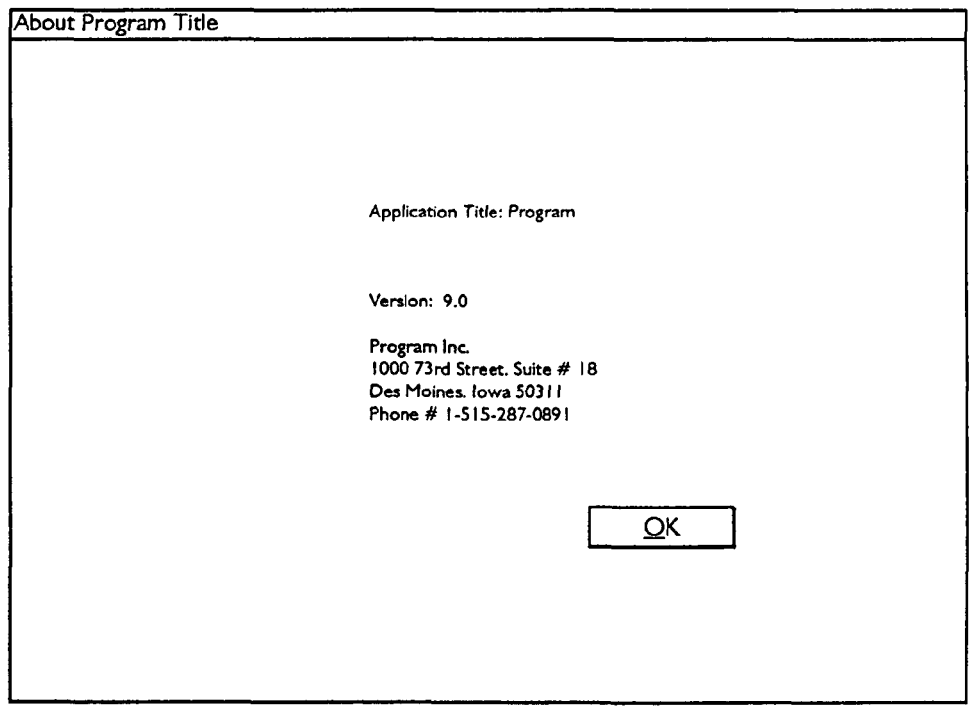
FIG. 31 is a pictorial representation of the Abort Program screen.

Now referring to FIG. 3 from the main menu 34, the care provider may select the about program option 44. Upon clicking on the about program option 54 push button, the about program option 54 screen is displayed as shown in FIG. 31. The screen displays the author of the program, the author's address and phone number, as well as the current version of the program. Once the care provider is done viewing this information, the care provider may return to the main menu 34 by selecting the OK option 218.

Once the care provider is finished using the front-end system 10, the care provider may log off using the log off option 46 from the main menu 34 as shown in FIG. 7. After logging off, the care provider exits the system 10 via exit 32.

The system 10 and program described above may be easily modified to work in other health care fields, such as dentistry and non-health care related fields such as accounting, law, architecture and others. Anyone in the multiple service industries could use the present invention for their billing and records system 10. For example, a law office, which bases its billing typically on a time standard, could easily use such a system 10. Instead of diagnosis codes, the law office would be able to use or codify commonly performed task categories, such as "telephone conversation," "briefing," "motion," "letter," "trial," etc. These categories could then have more specific sub categories. For instance, the category "motion" could have subcategories such as "summary judgment," "bifurcation," "compel," or as many others as should be desirable.

Much like the health care industry, more and more legal fees, such as court fees, administrative practice fees, etc. are constantly changing. Through the use of this billing/records system 10, a law office may have one person which can update all appropriate fees for the entire office. Simple modifications would be all that is required. Instead of patients, clients would be selected. Instead of referring physician, reference attorney or referring entity would be used. These and many other substitutions could be made to tailor the program to fit the needs of a law office. Similar modifications could be made to the program for use in an accounting office, insurance company, brokerage firm, or any other member of the multiple service industries doing business.

A general description of the present invention as well as a preferred embodiment of the present invention has been set forth above. Those skilled in the art to which the present invention pertains will recognize and be able to practice additional variations in the methods and systems described which fall within the teachings of this invention. Accordingly, all such modifications and additions are deemed to be within the scope of the invention which is to be limited only by the claims appended hereto.

What is claimed is:

1. A method for providing code-driven medical reporting for billing purposes, comprising:
   receiving a selection of a patient procedure code on a first computer, the patient procedure code representing a patient procedure performed on a patient during a patient encounter;
   receiving a selection of a plurality of diagnosis codes on the first computer, each of the plurality of diagnosis codes representing a diagnosis of the patient during the patient encounter;
   receiving a change in ordering of diagnosis codes from a user;
   linking the selection of the patient procedure code to the selection of the plurality of diagnosis codes on the first computer;
   documenting the linking of the selection of the patient procedure code and the selection of the plurality of diagnosis codes to provide for maintaining a user defined rank ordered relationship between the patient procedure code and the plurality of diagnosis codes based on the patient encounter to thereby provide a detailed record of the patient encounter.

2. The method of claim 1 wherein each of the plurality of diagnosis codes is an ICD code.

3. The method of claim 1 wherein the patient procedure code is a CPT code.

4. The method of claim 1 wherein a modifier is associated with the patient procedure code.

5. The method of claim 1 wherein a unit value is assigned to the patient procedure code.

6. A method for providing code-driven medical reporting, comprising:
   providing a user interface adapted for operation on a first computer;
   using the user interface to collect at least one procedure code representing a procedure performed on a patient during a patient encounter;
   for each of the at least one procedure code, using the user interface to collect a plurality of diagnosis codes, each of the plurality of diagnosis codes representing a diagnosis of the patient during the patient encounter to thereby establish a user defined link between each of the plurality of procedure codes and the plurality of diagnosis codes;
   using the user interface to reorder the plurality of diagnosis codes;
   documenting the patient encounter by storing each of the at least one procedure codes and storing each of the at least one diagnosis codes linked to each of the at least one procedure codes to provide a record of each set of diagnosis codes collected for each procedure code and a rank order of each set of diagnosis codes.

7. The method of claim 6 wherein the procedure code is a CPT code.

* * * * *